(12) United States Patent
Gerber

(10) Patent No.: US 6,291,723 B1
(45) Date of Patent: Sep. 18, 2001

(54) DIOLEFIN/HYDROXYARYL CONDENSATES AND CATALYST THEREFOR

(75) Inventor: Arthur H. Gerber, Louisville, KY (US)

(73) Assignee: Borden Chemical, Inc., Columbus, OH (US)

( * ) Notice: Subject to any disclaimer, the term of this patent is extended or adjusted under 35 U.S.C. 154(b) by 0 days.

(21) Appl. No.: 09/388,966

(22) Filed: Sep. 2, 1999

(51) Int. Cl.$^7$ .......................... C07C 37/14; C07C 39/06
(52) U.S. Cl. .................. 568/793; 568/628; 568/630; 568/632; 568/732; 568/733; 568/806; 528/205; 528/171
(58) Field of Search .................. 568/733, 793, 568/806, 732, 628, 630, 632; 528/205, 171

(56) References Cited

U.S. PATENT DOCUMENTS

| | | | |
|---|---|---|---|
| 4,394,497 | 7/1983 | Nelson et al. | 528/101 |
| 4,914,246 | 4/1990 | Oswald et al. | 568/793 |
| 4,927,905 | 5/1990 | Bogan | 528/205 |
| 4,973,764 | 11/1990 | Oswald et al. | 568/649 |
| 5,281,675 | 1/1994 | Hefner, Jr. et al. | 525/410 |
| 5,338,828 | 8/1994 | Hefner, Jr. et al. | 528/179 |
| 5,491,201 | 2/1996 | Hefner, Jr. et al. | 525/420 |
| 5,521,260 | 5/1996 | Futaesaku et al. | 525/502 |
| 5,607,890 | 3/1997 | Chen et al. | 502/202 |
| 5,663,470 | 9/1997 | Chen et al. | 585/520 |
| 5,739,377 | 4/1998 | Ohsawa et al. | 560/75 |

FOREIGN PATENT DOCUMENTS

05156134 * 6/1993 (JP) .

OTHER PUBLICATIONS

3M Fluorad, FC24, Product Information Bulletin, Jun. 1995.

"Reaction of Phenol with Endo–Dicyclopentadiene" V. Isagulyants et al. Neftekhimia (1974) 14(2), 280–3 —With English Translation.

Beilstein, RN 52062–67–6 Registry, Phenol, 4–(3a4,5,6,7,7a–hexahydro–4,7–methano–1H–inden–6–yl)–(9CI) (1998).

"Reaction of Phenol with Alkyl– and Alkenylcycloalkenes in the Presence of KU 23 Catalyst" Sadykhov, Sh. et al. Neftekhimiya (1996), 36(2), 158–168.

"Reaction of Phenol with Alkylcycloalkenes on a Zeolite-–Containing Aluminosilicate Catalyst" Soldatove, V. et al. Neftekhimiya (1988), 28(2), 189–99.

"Catalytic Alkylation of Phenol by Isoprene Dimers" Sadykhov. Sh. et al. Azerb. Neft. Khoz, (1984), (3), 46–9.

"Study of the O–Cycloalkylation of Phenol with Alkylcycloalkenes" Sadykhov, Sh. et al. Azerb, Khim Zh. (1978), (2), 35–7.

"Use of Ion Exchange Resins in Catalysis, Reaction of Dicyclopentadiene with phenol on a KU 2 Cation Exchanger" Isagulyants, V. et al., Zh. Prikl. Khim. (Leningrad) (1974) 47 (3), 684.

H. A. Bruson, et al.; J. Am. Chem. Soc. 68, 8 (1946) pp. 8–10.

* cited by examiner

*Primary Examiner*—Sreeni Padmanabhan
(74) *Attorney, Agent, or Firm*—George P. Maskas; Kenneth P. Van Wyck

(57) ABSTRACT

A catalyst composition comprising trifluoromethanesulfonic acid (also referred to as triflic acid) and a sufficient quantity of a substance (also referred to as a retarder) to decrease but not eliminate the catalytic activity of the acid is disclosed. Also disclosed, is a method and composition for condensing a hydroxyaryl with a diene by use of the catalyst composition. The method is capable of producing condensates having: a mole ratio of 1 mole of the diene to one mole of the hydroxyaryl; one mole of diene to two moles of the hydroxyaryl as well as higher molecular weight products such as resins by changes in temperature, time of reaction, type and quantity of retarder and other variables.

33 Claims, No Drawings

DIOLEFIN/HYDROXYARYL CONDENSATES AND CATALYST THEREFOR

FIELD OF INVENTION

This invention relates to condensation products of a hydroxyaryl and a diolefin, the method for preparation of such products as well as a catalyst system used for their preparation. More particularly, this invention relates to such condensation products and their method of manufacture in the presence of a catalyst composition containing trifluoromethanesulfonic acid (triflic acid) and a substance in an amount which decreases without eliminating the catalytic activity of the acid, said substance is also simply referred to as a retarder.

It has now been found that the reaction of a hydroxyaryl with a non-conjugated diene in the presence of both triflic acid and a retarder will produce products which are substantially different from such reaction without the use of the retarder. Broadly, the use of the retarder provides products which have lower molecular weights such as solids, crystalizable and non-crystalizable liquids having a wide range of viscosities. The retarder is a material which at certain concentrations in relation to the triflic acid decreases, without eliminating, the catalytic activity of the triflic acid. The retarders are generally about neutral to slightly basic in pH. The retarder acts as a base in relation to the triflic acid.

BACKGROUND OF THE INVENTION

The prior art shows the use of trifluoromethanesulfonic acid (triflic) acid as a catalyst for various hydrocarbon conversion processes but such prior art fails to suggest the instant invention. Some prior art patents involving the use of triflic acid as a catalyst or the preparation of condensation products from a diene and a hydroxyaryl are set forth below.

U.S. Pat. No. 4,973,764 of Nov. 27,1990 to A. Oswald et al discloses the use of triflic acid as an alkoxylation catalyst.

U.S. Pat. No. 5,521,260 of May 28, 1996 to N. Futaesaku et al discloses the use of triflic acid as a polymerization catalyst for thermosetting resins.

U.S. Pat. No. 5,607,890 of Mar. 4, 1997 to F. J. Chen et al discloses heterogeneous catalysts having certain insoluble triflic acid salts on an inorganic oxide support for catalyzing hydrocarbon conversion reactions including alkylation and polymerization. As suitable monomers for the conversion reactions a wide variety of olefins and carbocyclic aromatic compounds are mentioned. Monomer feed streams for polymerization are substantially free of impurities which may adversely affect polymerization such as basic and nitrogen materials. Lower alcohols along with organic acids are mentioned as catalyst promoters.

U.S. Pat. No. 5,663, 470 of Sep. 2, 1997 to F. Chen et al discloses a heterogeneous catalyst system comprising a solid state insoluble salt catalyst for polymerization and alkylation of olefinic monomers in the presence of a polar or non-polar reaction medium which comprises: (a) a solid state catalyst component of at least one salt of a strong acid and certain transition metals wherein the salt is insoluble in the reaction medium; and (b) a cocatalyst for promoting the polymerization. The salt of a strong acid includes that of triflic acid. Monomers include a wide variety of olefins and carbocyclic aromatic compounds. The enumeration of cocatalyst includes water, alcohols such as the lower alkanols, e.g., methanol, and Bronsted acids such as triflic acid or Lewis acids. This 470 patent of Chen et al describes triflic acid, water and methanol as catalyst reaction promoters. However, in, the catalyst system of the instant invention, water and alcohols, e.g., methanol are catalyst suppressors in that water and methanol both act as catalyst retarders instead of promoters. Although the applicant does not wish to be held to any theory, it is believed that water as well as methanol in contact with the insoluble catalyst salts of Chen et al cause dissociation of the salts which in turn promote the catalytic reaction.

3M Product Information Bulletin of 6-95 entitled "Fluorochem" discloses various properties and uses of triflic acid, e.g., the use of triflic acid as a catalyst in alkylation and polymerization reactions as well as some physical or chemical properties of mixtures of triflic acid with water or ethers.

Neftekhimiya, 1974, Volume XIV, No. 2, 280–283 (Russian) discloses the reaction of phenol with clicyclopentadiene in the presence of about 10% to 50% by weight, based on the weight of both monomers, of a cation exchange resin catalyst for the preparation of compounds, such as prepared in the instant invention, including some resin.

H. A. Bruson, et al., J. Amer. Chem. Soc. 68, 8 (1946), pp 8–10, shows the preparation of aryloxy-dicyclopentadiene compounds from hydroxyaryls and dicyclopentadiene in the presence of various acids.

SUMMARY OF THE INVENTION

In one aspect, this invention relates to a method for condensing a hydroxyaryl with a non-conjugated diene in the presence of a catalyst composition comprising trifluoromethanesulfonic acid (triflic acid) and a substance in a quantity which decreases without eliminating the catalytic activity of the acid .

In another aspect, this invention relates to a catalyst composition comprising triflic acid and a substance in a quantity which decreases without eliminating the catalytic activity of the acid and which does not react with a double bond of a non-conjugated diene.

In still a further aspect, this invention relates to a composition comprising a hydroxyaryl, a non-conjugated diene, trifloromethanesulfonic acid and a substance in a quantity which decreases without eliminating the catalytic activity of the acid and which does not react with a double bond of the diene.

In yet another aspect, this invention relates to a method for condensing a hydroxyaryl with a non-conjugated diene in the presence of a catalyst system comprising trifluoromethanesulfonic acid and a substance in a quantity which decreases without eliminating the catalytic activity of the acid and which does not react with a double bond of the diene to prepare condensates having one mole of diene bound with one mole of a hydroxyaryl, condensates having two moles of the hydroxyaryl bound with one mole of the diene, as well as higher molecular weight products, including resins.

In a further aspect, this invention relates to condensing a hydroxyaryl with a non-conjugated diene in the presence of a catalyst system comprising trifluoromethanesulfonic acid and a substance in a quantity which decreases without eliminating the catalytic activity of the acid while controlling the molecular weight, viscosity and other properties of the products produced over time and/or temperature variations.

In yet additional aspects, this invention relates to compositions of a hydroxyaryl and an non-conjugated diene, as well as their method of manufacture, for producing: (A) a condensation product of a hydroxyaryl and a non-conjugated diene wherein the ratio of aryloxy-non-conjugated-diene compound to hydroxyaryl-non-conjugated-diene compounds is about 0.5 to 1.5 and from about 40% to at least 90% of the product, preferably 40% to at least 95% of the product is that of both the aryloxy-diene compound and the hydroxyaryl-diene compound; (B) a condensation product of a hydroxyaryl and a non-conjugated diene wherein the product contains at least 90% of aryloxy-non-conjugated-diene compound and hydroxyaryl-non-conjugated-diene compound and less than about 5% of higher molecular weight products of the condensation; and (C) a condensation product having a maximum content of about 2% of aryloxy-non-conjugated-diene compound, from about 5% to 40% of hydroxyaryl-non-conjugated-diene compounds with the remainder being higher molecular weight products of the condensation reaction.

DETAILED DESCRIPTION OF THE PREFERRED EMBODIMENTS

In the broad method of this invention, the non-conjugated diene is typically contacted with a hydroxyaryl at an elevated temperature in the presence of the triflic acid and retarder for a time sufficient to react the hydroxyaryl with the diene. Completion of the reaction can be evidenced by gas chromatographic monitoring of the diene or consistency of refractive index of the reaction mixture or by measurements of the solution viscosity during reaction after developing a correlation between the solution viscosity and the desired product viscosity. Typically, in conducting the reaction, a hydroxyaryl, triflic acid and the retarder are mixed and preheated. The diene is then added to the mixture. Optionally, the diene can also be preheated. When phenol is used as the hydroxyaryl a typical pH (25° C.) for a solution of 0.05% triflic acid in the phenol is about 1.1 to about 1.2 as measured in 2.5 g of acidified phenol dissolved in 25 milliliters (ml) of methanol.

Upon completion of the reaction, the triflic acid can be removed, e.g. neutralized or washed out of the reaction mixture since it is water soluble, to recover the product. In neutralizing the acid, the pH of the reaction mixture is preferably neutralized to a pH of 7 or more such as 7.5 or 8 since even a slight amount of un-neutralized triflic acid can cause further changes in the final product, particularly upon heating such as in the removal of excess hydroxyaryl from the reaction mixture. Nevertheless, the acid need not be entirely removed from the reaction mixture. Illustratively, the reaction mixture can be brought up to a pH of about 4 to about 6 instead of complete neutralization. Neutralization of the reaction mixture to a pH such as that of about 4 to about 8 is accomplished by means well known in the art such as by addition of an alkali or alkaline earth oxide, hydroxide or carbonate or by very basic amines such as triethylamine, triethylene diamine, etc.

The temperature and time of reaction are those which are sufficient to effectuate the preparation of the desired product. This will depend on the monomers employed, the quantity of catalyst and retarder, as well as the type of retarder being used. The reaction temperature will typically vary over a wide range such as that of about 35° C. to about 190° C. and preferably from about 45° C. to about 130° C. Reaction time can vary over a wide range such as that of about 1 to about 15 hours or more, preferably about 4 to 8 hours. To facilitate reaction at temperatures below about 45° C. techniques which liquify a solid hydroxyaryl such as the following can be used: (1) diluting the hydroxyaryl with small amounts, e.g., about 5% of an inert solvent such as an aromatic hydrocarbon, e.g., toluene, xylene, etc. or chlorinated solvent or by (2) adding a small quantity, e.g. about 5% of non-conjugated diene at 42° C. to 45° C. and then lowering the reaction temperature.

A versatile process for preparing, in good yield, liquid dicyclopentadiene/phenol condensates varying in viscosity from about 600 cps (25° C.) to about 20,000 cps (25° C.) as well as some solid condensates comprises:

(a) adding the diene over one to three hours at about 40° C. to abut 70° C. to phenol (diene/phenol mole ratio about 0.4–0.5) in the presence of about 0.03% to 0.08% each, based on the weight of the phenol, of triflic acid and N-methyl pyrrolidone;

(b) further maintaining the above temperature for about one to three hours;

(c) increasing the temperature to abut 80° C. for about one to ten hours (higher temperatures and longer hold times increase viscosity and molecular weight);

(d) neutralizing the catalyst with a basic material; and (e) removing phenol by distillation. With a 0.45 mole ratio of diene to phenol and a viscosity of 600 cps (25° C.) or higher, no detectable diene was found (i.e., not greater than 0.1%) by the above versatile method. The reaction can be monitored by solution viscosity and/or refractive index, except for solid condensates.

The use of the retarder with the triflic acid enables the preparation of condensates having different properties as compared to the use of triflic acid alone under the same reaction conditions. Thus, when the retarder is present: the condensates have a lower molecular weight and lower viscosity; also, low viscosity crystalizable liquids, e.g., products having a viscosity of about 200 to about 600 cps at 25° C. can be prepared as well as stable liquids with broad viscosity ranges such as that of from about 600 or 700 to about 120,000 cps at 25° C. and preferably stable liquids having a viscosity range of about 700 to 20,000 cps at 25° C. Additionally, monomeric compounds can be prepared.

The Hydroxyaryl

The hydroxyaryl is an aromatic, carbocyclic hydroxyl-containing compound. Suitable hydroxyaryls include, for example, those compounds which contain one or two aromatic rings, one or two aryl hydroxyl groups and at least one ortho or para ring position of the aryl with respect to a hydroxyl group or groups available for alkylation. Suitable hydroxyaryls which can be employed herein include, for example, phenol, methoxyphenol, phenoxyphenol, naphthol, dimethylphenol, o-cresol, m-cresol, p-cresol, hydroquinone, catechol, resorcinol, guaiacol, pyrogallol, phloroglucinol, isopropylphenol, ethylphenol, propylphenol, t-butyl-phenol, octylphenol, nonylphenol, cumylphenol, p-phenylphenol, o-phenylphenol, m-phenylphenol, bisphenol-A, bisphenol-F, dihydroxy-diphenyl sulfide, mixtures thereof and the like. Preferred hydroxyaryl compounds include: phenol itself; cresol, particularly meta-cresol; resorcinol; and bisphenol-A. Hydroxyaryls often contain small quantities of water. It is preferred that the hydroxyaryl reactant contain no more than about 0.1% by weight and particularly not more than about 0.06% by weight of water. Mixtures of the various hydroxyaryls can also be employed.

The Diene

Illustrative of the of non-conjugated dienes usable in this invention there can be mentioned: various hydrocarbon dienes such as: straight chain acyclic dienes; branched chain acyclic dienes; single ring cyclic dienes; multi-ring cyclic fused and bridged ring dienes; cycloalkenyl-substituted alkenes; and dialkenyl benzenes.

Preferred non-conjugated dienes are those having from about 6 to about 15 carbon atoms such as: 1,6-octadiene; dicyclopentadiene; methyl dicyclopentadiene; dimethyl dicyclopentadiene, limonene and dipentene. The dienes can be in any of their isomeric forms such as: endo- or exodi-cyclopentadiene; dextro-limonene, and the like. Mixtures of the dienes can be used. Illustratively, of such mixtures there can be mentioned those containing two or more of the following: dicyclopentadiene, methyl cyclopentadiene dimer, limonene, dipentene, 5-ethylidene -2-norbornene, 2,5-dimethyl-1,5-hexadiene, and 1,5-cyclooctadiene.

Illustrative of specific dienes, there can be mentioned: 1,4 hexadiene; 1,6 octadiene; 5-methyl-1,4-hexadiene; 3,7-dimethyl-1,6-octadiene; 3,7-dimethyl-1,7-octadiene; 1,4-cyclohexadiene; 1,5-cyclooctadiene and 1,5-cyclododecadiene; tetrahydroindene, methyl-tetrahydroindene; cyclopentadiene; dicyclopentadiene; cyclopentadiene trimer, methyl cyclopentadiene dimer; limonene; bicyclo-2.2.1-hepta-2,5-diene; alkenyl, alkylidene, cycloalkenyl and cycloalkylidene norbornenes such as 5-methylene-2-norbornene, 5-ethylidene-2-norbornene, and 5-vinyl-2-norbornene; divinyl benzene; diisopropenyl benzene; allyl cyclohexene, vinyl cyclooctene, allyl cyclodecene, and vinyl cyclodecene. Suitable unsaturated substances also include other dimers, trimers, tetramers and oligomers of the aforementioned dienes.

The methods of this invention are also suitable for reacting a hydroxyaryl with a mixture of non-conjugated diene or such non-conjugated diene with a minor quantity of a conjugated diene. In such case, it is preferred that the conjugated diene not exceed about 5% by weight of the total weight of the dienes to be reacted. The conjugated dienes can have various degrees of unsaturation such as mono-, di-, and triolefinic unsaturation. Illustrative of the conjugated dienes there can be mentioned: isoprene, piperylene. 2,5-dimethyl-2,4-hexadiene, cyclopentadiene, 2,6-dimethyl-2,4, 6-octatriene (alloocimene), and the like.

The molar ratio of the non-conjugated diene charged in the reaction mixture of this invention is generally about 0.1 to 0.8 moles of diene for each mole of hydroxyaryl, and preferably about 0.2 to about 0.6 moles of diene for each mole of hydroxyaryl and particularly about 0.25 to about 0.5 moles of diene for each mole of hydroxyaryl.

The Substance which Decreases but Does Not Eliminate the Catalytic Activity of the Acid (Also Referred to as Retarder)

The substance in a quantity which decreases without eliminating the catalytic activity of the acid (also referred to as retarder) used in conjunction with trifluoromethane-sulfonic acid (triflic acid) in the condensation of a hydroxyaryl with a non-conjugated diene provides desirable unexpected properties, particularly condensation products which are non-crystalizing liquids with broad viscosity ranges. Illustratively, the presence of N-methyl pyrrolidone (NMP) in sufficient quantity to decrease without eliminating the catalytic activity of the triflic acid in the reaction of a hydroxyaryl and a non-conjugated diene exerts a marked effect on product properties. The absence of NMP in the reaction mixture gives products having significantly higher viscosity, higher molecular weight and higher combining weight of hydroxyaryl to the diene. Compositions prepared by the reaction of a hydroxyaryl and a non-conjugated diene by this invention can yield: 1:1 molar condensation compounds of a hydroxyaryl and a non-conjugated diene. This indicates the preferential selectivity of one of the diene double bonds in the reaction. In addition the reaction can produce bis(hydroxyaryl)-non-conjugated-diene compounds as well as resins.

The retarders are substances which, in the proper amount, decrease but do not eliminate the catalytic activity of the acid. Many retarders are slightly acidic, neutral or slightly basic materials and, if soluble in water, will have a pH of about 6 to about 7.5. However, some of the retarders are not soluble in water. Typically, the retarder acts as a weak base in relation to the triflic acid. The quantity of retarder used is sufficient to lower the catalytic activity of the acid without eliminating such catalytic activity. It is believed that the lowering of the catalytic activity is due to the retarder coordinating electrons with triflic acid and that the retarder acts as a base in relation to the acid. The retarder substance can be a single compound, a mixture of compounds or substances including a polymer such as those derived from N-vinyl-2-pyrrolidone and N-vinylcaprolactam wherein the polymer can be a part of the liquid phase, e.g., soluble, in the reaction mixture or a solid, e.g., cross-linked. The cross-linked polymers lead to heterogeneous catalysis and generally will require higher reaction temperatures and/or longer reaction times in relation to the use of the corresponding soluble polymer retarder. One advantage of the insoluble retarder is that it can be removed by filtration.

Illustrative of various types of retarders there can be mentioned water and organic compounds such as; alcohols; ethers; and nitrogen containing compounds such as those containing from about 4 to 23 carbon atoms and 1 to 3 nitrogen atoms., The retarders can also contain more than one chemical functionality, e.g., they can be both ethers and organic nitrogen containing compounds. Each of the retarders can be used alone or in combination with another retarder.

Illustrative of organic nitrogen containing retarders there can be mentioned amines, amine N- oxides, amides, amino acids, all of which can be straight chain, aromatic or cycloaliphatic nitrogen containing substances. When the retarder is an amine it will typically have a $PK_a$ value of not greater than about 1.2 such as that of about −2.0 to about 1.2 (for comparison, the $PK_a$ of pyridine is 5.25). Suitable organic nitrogen retarder substances include: acyclic amides such as N,-di(lower alkyl)amides, e.g., N,N-dimethylacetamide; cyclic amides such as e-caprolactam (2-oxohexamethyleneimine) and 2-pyrrolidone; N-substituted derivatives thereof such as N-(lower alkyl) pyrrolidone, e.g., N-methyl or N-ethyl pyrrolidone; cycloalkylpyrrolidones such as N-cyclohexyl pyrrolidone; as well as other organic nitrogen substances as will be mentioned hereafter.

Organic retarder nitrogen containing substance can be a cyclic amide such as those which can be represented by the formula:

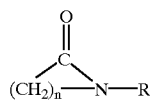

wherein n is an integer of about 3 to 5 and R is hydrogen, alkyl of 1 to 12 carbon atoms, phenyl, cyclohexyl, alkylaryl such as benzyl, etc.

In addition, other retarder amides include acylated aromatic amines such as those represented by the formula:

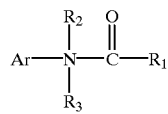

wherein $R_1$ is lower alkyl or phenyl, $R_2$ is hydrogen or lower alkyl, and $R_3$ is lower alkyl and Ar is phenyl, tolyl, xylyl, or naphthyl. As elsewhere in this application, the term lower in relation to an aliphatic group relates to such group having from 1 to 4 carbon atoms.

Representative of acylated arylamide retarders there can be mentioned acetanilide, chloroacetanilide, formanilide, and N-methylformanilide. Still other amide retarders are represented by aromatic amides and their N-lower alkyl derivatives of the formula:

wherein Ar is aryl, e.g., phenyl and each of $R_1$ and $R_2$ is hydrogen or lower alkyl.

The amine retarders can be aliphatic or aromatic compounds. As suitable amine retarders there can be mentioned: 2-halopyridines such as that of chloro-, fluoro- and bromopyridine; 2-haloquinolines; 4-nitroaniline; quinoxaline, pyrazine; and 3-nitropyridine. Additional amine retarders together with their pKa values as shown in parenthesis include: N-cyanodiethylamine (−2.0); 1-amino-2-nitronaphthalene (1.74); 4-chloro-2-nitroaniline (−1.02); dicyanomethyl ethyl amine (−0.6); 2-fluoropyridine (−0.44); 2-nitroaniline (−0.26); bis(cyanomethyl) amine (0.2); 2-chloropyridine (0.49); 1-amino-4-nitronaphthalene (0.54); quinoxaline (0.56); N,N-dimethyl-4-nitroaniline (0.607); pyrazine (0.65); diphenylamine (0.79); 3-nitropyridine (0.81); 2-bromopyridine (0.90); 2-cyanoaniline (0.95); 2,6-dimethyl-4-nitroaniline (0.98); 4-nitroaniline (1.00); 2-methyl-4-nitroaniline (1.04); 2-bromoquinoline (1.05); acetanilide (0.4); pyridine N- oxide (0.69); picoline N-oxide (1.03); and tris(2-cyanoethyl)amine (1.1). The term "(lower alkyl)" as used in this application means an alkyl group of 1 to 4 carbon atoms. The retarders which are ethers can be aliphatic, cyclic, di- or triethers, or aromatic ethers. The cyclic ethers can be cycloaliphatic or substituted aromatic ethers such as lower alkoxy substituted phenyls. When ethers are employed as retarders, they are preferably used at lower reaction temperatures such as from about 35° C. to about 60° C. since at higher temperatures, e.g., 80° C., some low molecular weight ethers, e.g., diethyl ether, are degraded by the triflic acid, e.g., diethyl ether is degraded to ethyl ester and ethylene. Ethers do not appear to be as effective as other retarders. Representative acyclic ethers include: di-n-propyl and di-n-butyl ether, 1,2-dimethoxyethane; bis(2-methoxyethyl) ether; as well as lower alkoxy terminated polyols such as polyethylene and polytetramethylene glycols, particularly those wherein each alkylene group contains from 2 to 4 carbon atoms and the alkoxy group contains from 1 to 4 carbon atoms. Cyclic ethers can be represented by: 1,4-dioxane; tetrahydrofuran and alkylated derivatives thereof. Aromatic ethers include anisole and phenetole. The ethers can also be ether alcohols. Illustrative of ether alcohols there can be mentioned mono-lower-alkoxy ethers derived from ethylene, propylene, diethylene, polyethylene glycols and 2-phenylethanol. The ethers can contain sulfur instead of oxygen. Illustrative of sulfur containing ethers there can be mentioned tetrahydrothiophene. Some substances containing an ether linkage also contain nitrogen , e.g., ether amides.

Representative of amino acid retarders there can be mentioned: sulfanilic, anthranilic, picolinic, proline, sarcosine, serine, 3-phenyl-alpha-alanine, taurine, and N-alkylated derivatives thereof.

Preferred ether amides are those of the formula:

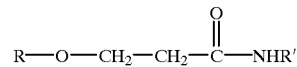

wherein each of R and R' is alkyl of 1 to about 10 carbon atoms.

The retarders used in this invention include alcohols such as monohydric, dihydric and polyhydric alcohols. Illustrative of monohydric alcohols there can be mentioned, primary alcohols, such as aliphatic acyclic and cyclic alcohols of one to about 10 carbon atoms, e.g., methanol, ethanol, 2-phenylethanol, 2-phenoxyethanol and cyclohexylmethanol. The primary alcohols such as methanol and ethanol are known to attack diene double bonds in the presence of a strong acid and therefore are not among preferred retarders. Illustrative of the dihydric alcohols there can be mentioned glycols such as: ethylene glycol; 1,4-butanediol, 1,4-cyclohexane dimethanol, diethylene glycol and polyalkylene glycols, particularly those wherein the alkylene group has from 2 to 4 carbon atoms in each alkylene group. The alcohols can also have ether functionality such as with ether alcohols as mentioned hereinabove.

Water is a suitable retarder in the instant catalyst compositions. However, water is known to cause some hydroxylation of diene double bonds and therefore is not among preferred retarders. When it is desired to minimize or eliminate the effect of water, the reaction mixture will be substantially free of water.

Preferred retarders include: acetanilide; bis(2-methoxyethyl)ether; N-methyl pyrrolidone; 2-chloropyridine; poly(2-vinyl pyrrolidone); N-cyclohexyl pyrrolidone; and 2-nitroaniline.

Solvents

Generally, the reaction is conducted without a solvent. If a solvent is used, it should be an inert solvent which does not contain oxygen such as toluene, chlorobenzene, or xylene.

The Catalyst Composition

The catalyst composition comprises trifluoromethanesulfonic acid (triflic acid) and the retarder. The triflic acid is a liquid with a boiling point of 162° C. The catalyst composition comprising the triflic acid and retarder can be a homogeneous catalyst composition wherein the triflic acid and the retarder are in the liquid state or soluble in the reaction mixture. On the other hand, the catalyst composition can also be a heterogeneous catalyst system wherein the retarder is insoluble, e.g, a solid, such as cross-linked polymers of those mentioned above. Illustrative of solid and insoluble retarders cross-linked polymers there can be mentioned POLYCLAR 10 which is sold by ISP Technologies of Wayne, N.J.

The Quantity of Triflic Acid and the Retarder

The quantity of the trifloromethanesulfonic acid (triflic acid) and retarder in the reaction mixture is in an amount sufficient to effectuate the desired reaction. The quantity of triflic acid catalyst will generally vary from about 0.01% to about 1% based on the quantity of hydroxyaryl and preferably about 0.03% to 0.15% by weight of the hydroxyaryl. The quantity of the retarder will generally vary from about 0.5 to about 10 parts for each part of the triflic acid, by weight, and preferably about 1 to 3 parts of the retarder for each part by weight of the triflic acid. Also, the quantity of retarder based on the weight of hydroxyaryl will typically vary from about 0.01% to about 1% and preferably about 0.03 to about 0.3%. The lower the concentration of the retarder in relation to the acid, the faster will be the reaction. The retarder provides a practical way for slowing down the reaction so that products of the reaction which ordinarily may be evanescent can be detected and recovered. Larger quantities of the triflic acid together with corresponding larger quantities of the retarder can be used but this becomes uneconomical and would increase the amount of catalyst residue.

The principal quantity of monomeric compounds which are produced by this invention fall under three categories. In the first category, one mole of the hydroxyaryl reacts with one mole of the non-conjugated diene to produce an aryloxy-non-conjugated-diene compound wherein the aryl and the diene reactants are joined through the oxygen of a hydroxy group of the aromatic compound, i.e. production of an ether compound. In the second category, one mole of the hydroxyaryl reacts with one mole of the non-conjugated diene to produce a hydroxyaryl-non-conjugated-diene compound wherein the aryl and the diene reactants are joined through a carbon to carbon linkage and the hydroxy group of the aryl carbocyclic ring bound to the diene can be in either the para or ortho position on the reacting carbocyclic aromatic ring of a monohydric aromatic compound. In the case the hydroxyaryl has two hydroxyl groups on the same aromatic ring or on different aromatic rings, the bonding of the reactants is again through a carbon to carbon linkage of an aromatic ring and the diene. The (a) aryloxy-non-conjugated-diene compound and the (b) hydroxyaryl-non-conjugated-diene compound wherein the hydroxy group of the aryl ring bound to the diene residue is in the para, ortho, or both positions, are referred to herein as 1:1 molar condensation products since one mole of the diene combines with one mole of the hydroxyaryl. In the third category, two moles of the hydroxyaryl react with one mole of the non-conjugated diene wherein each of the two unsaturated groups of the diene are the location for carbon to carbon bonding of an aryl carbocyclic ring of each hydroxyaryl and the diene to produce a bis(hydroxyaryl)-non-conjugated-diene compound. In addition to the monomers resinous material is also produced.

The above reactions can be better understood by the below schematic reaction of phenol with dicyclopentadiene which is referred to as Equation A and which is also shown in the Russian reference: Neftekhimiya, 1974, Volume XIV, No. 2, 280–283, page 281 which reference is incorporated herein by reference in its entirety.

As shown below in Equation A, when phenol is reacted with dicyclopentadiene in the presence of an acid, a reaction of one mole of phenol with one mole of dicyclopentadiene occurs via the unsaturated bond in the bicyclo (2,2,1) heptene ring to produce either a phenoxy-dicyclopentadiene (i.e., an ether) or a phenol-dicyclopentadiene compound. In the case of the phenol-dicyclopentadiene compound, the phenolic hydroxyl group of the bonding aryl ring is in the ortho or para position so that the bonding between the phenol and dicyclopentadiene residues is through a carbon to carbon bond. Also, 2 moles of the phenol react with one mole of dicyclopentadiene to produce a bis(phenol) dicyclopentadiene compound wherein both of the unsaturated bonds of the diene react with the two phenol molecules to again provide a carbon to carbon linkage of the phenol and dicyclopentadiene residues. In the reaction, if an endo-dicyclopentadiene is used, it converts to the exo-configuration during the reaction whereas, if the exo-configuration is the starting material, it remains as the exo-configuration during the reaction. The reaction of the phenol with the dicyclopentadiene can be represented as shown below in Equation A wherein: "I" represents a hydroxyaryl, specifically phenol and "II" represents a non-conjugated diene, specifically endo-dicyclopentadiene. The products of the condensation reaction are as follows wherein: "III" represents the aryloxy-non-conjugated-diene, specifically, phenoxy-exo-dicyclopentadiene; "IVA" and "IVB" represent a para or an ortho hydroxyaryl-non-conjugated-diene, specifically, hydroxyphenyl-exo-dicyclopentadiene wherein the IVA compound has the hydroxyl group in the ortho position of the phenyl ring and the IVB compound has the hydroxy group in the para position of the phenyl ring.; and: "V" represents a bis (hydroxyaryl)-non-conjugated-diene, and specifically, bis (hydroxyphenyl)-exo-dicyclopentadiene. In the below reaction the specific residue of the hydroxyaryl produced in the reaction is that of phenol. In like manner, the specific residue of the hydroxyaryl produced in the reaction can be that of a cresol, bisphenol-A, resorcinol, etc. when the respective hydroxyaryl is used as the starting material, e.g., when the hydroxyaryl is resorcinol, the hydroxyaryl residue of an aryloxy-non-conjugated-diene reaction product will be that of resorcinol, e.g., the resorcinol linked to the diene through one of the oxygen atoms.

invention can produce a reaction product wherein the ratio of aryloxy-non-conjugated-diene compound to hydroxyphenyl-non-conjugated-diene compound, e.g., phenoxy-dicyclopentadiene compound to phenol-dicyclopentadiene compound is about 0.5 to about 1.5. The above ratios of aryloxy-diene compound to hydroxyaryl-diene compound, e.g., phenol-dicyclopentadiene compound are unexpected in light of the Russian reference. For example, products in Table 1 of the Russian reference under Equation A

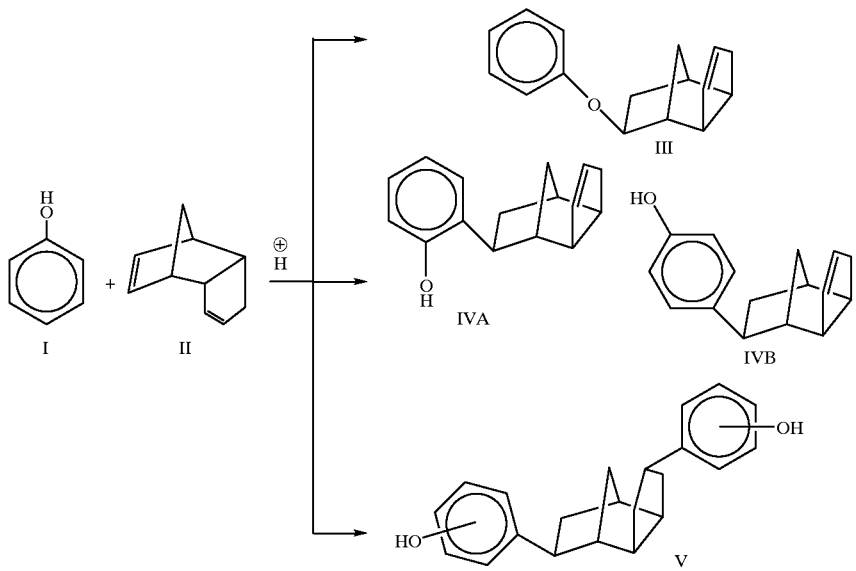

The quantity of aryloxy-non-conjugated-diene compound decreases at higher temperature and prolonged heating. Milder conditions of reaction produce more of the aryloxy-non-conjugated-cliene compound (ether) whereas higher temperatures and prolonged heating cause the reaction to produce increased quantities of the hydroxyaryl-non-conjugated-diene compounds, bis(hydroxyaryl) products, additional higher molecular weight products and increasing quantities of resinous materials.

The viscosity and molecular weight of the previously neutralized condensation product from the reaction of this invention using the triflic acid can be increased by heating with an acid. Such acid is preferably a volatile or thermally decomposable strong acid, e.g., oxalic or trichloroacetic acid. The levels of acid which can be employed are about 0.2 to about 2% based on the weight of the condensate and suitable temperatures are about 130° C. to about 180° C. The advantage of using a volatile or thermally decomposable acid is that the resulting product does not contain additional impurities, e.g., neutralized catalyst.

Depending on reaction conditions, compositions produced by the method of this invention can contain ratios of various compounds which are substantially and unexpectedly different from those in the prior art such as the above Russian reference. Also, the method of this invention can prepare certain of the compounds in substantial exclusion of the others of the type shown in the mixture of compounds of the Russian reference. Illustratively, the method of this a variety of conditions give ratios of 2.06 to 5.12 of the phenoxy-dicyclopentadiene compound to the phenol-dicyclopentadiene compounds. Products in Table 2 of the Russian reference give ratios of infinity, zero and 13.4 of the phenoxy-dicyclopentadiene compound to phenol-dicyclopentadiene compounds.

Condensation products having the 0.5 to 1.5 ratio of aryloxy-non-conjugated-diene compound, e.g., phenoxy-dicyclopentadiene to hydroxyaryl-non-conjugated-diene compound, e.g., phenol-dicyclopentadiene compound include: products having a viscosity of about 700 to 120,000 cps at 25° C. The lower viscosity products provide for better wetting of aggregates and fibers as well as the preparation of lower viscosity reaction products with epoxy compounds.

Some of the condensates produced when hydroxyaryl is reacted with dicyclopentadiene in this invention are supercooled liquids, i.e. normally solid products which are in the liquid state at a temperature below their melting point. In time these materials will typically solidify as in the case of supercooled liquids generally. However, compositions of the supercooled liquids of this invention have been observed to remain in the liquid state for hours, days or even weeks.

At least three different types of condensation products which are mixtures of the reaction products, e.g., compounds and typically some resin are produced by this invention which have novel and unobvious quantities and ratios of the condensation products. These three types are designated as Group A, B, and C condensation products below. Group A products are that of a condensation product of a hydroxyaryl and a non-conjugated diene wherein the ratio of the resulting aryloxy-non-conjugated-diene compound to resulting hydroxyaryl-non-conjugated-diene compound is about 0.5 to 1.5 and from about 40% to at least 90%, preferably 95% of the product by weight is that of both the aryloxy-non-conjugated-diene compound and hydroxyaryl-non-conjugated-diene compound whereas about 5% by weight to 60% by weight is that of products of the condensation reaction having molecular weights higher than the hydroxyaryl-non-conjugated-diene compound. The Group A compositions are liquids with a viscosity of about 700 to 120,000 cps at 25° C. and preferably have a viscosity of from about 700 to 20,000 cps at 25° C.

The Group A condensation product can be prepared by making a condensation product of a hydroxyaryl and a non-conjugated diene, by: (a) reacting the diene with a hydroxyaryl at a mole ratio of 0.2 to about 0.5 moles of the diene for each mole of the hydroxyaryl at a temperature of about 45 to about 100° C. and (b) conducting the reaction in the presence of about 0.03% to about 0.1% of triflic acid based on the weight of hydroxyaryl and about 0.03 to about 0.3 of N-methyl pyrrolidone based on the weight of hydroxyaryl, provided that the quantity of the N-methyl pyrrolidone is at least equal to the amount of triflic acid.

The Group B condensation product of a hydroxyaryl and a non-conjugated diene are those wherein the product contains at least 90% and preferably at least 95% by weight of aryloxy-non-conjugated-diene and hydroxyaryl-non-conjugated-diene compound and less than about 10%, preferably less than about 5%, of higher molecular weight products of the condensation reaction. The ratio of aryloxy to hydroxyaryl compounds in Group B is about 18 to about 48 by weight and the ratio of said aryloxy and hydroxyaryl compounds to products of the condensation reaction having a higher molecular weight than said aryloxy or hydroxyaryl compounds is at least 9 to 1 by weight. Condensation products of Group B can be prepared by (a) reacting a non-conjugated diene with a hydroxyaryl in a mole ratio of about 0.3 to 0.5 of non-conjugated diene to hydi-oxyaryl and at a temperature of about 40° to 70 ° C. in the presence of,
  (1). about 0.03% to about 0.1% of triflic acid based on the weight of hydroxyaryl; and
  (2). about 0.0% to about 0.3% of N-methyl pyrrolidone based on the weight of hydroxyaryl, provided that the quantity of the pyrrolidone is at least equal to the quantity of triflic acid. When phenol and dicyclopentadiene are the reactants, the Group B compositions can have a viscosity of about 200 to 400 cps at 25° C. generally as supercooled liquids.

Group C condensation product is that of a hydroxyaryl and a non-conjugated-diene wherein the product contains not more than about 2% of aryloxy-non-conjugated-diene compound, from about 5% to about 40%, preferably 30%, of hydroxyaryl-non-conjugated-diene compound by weight and the remainder being essentially (substantially all) higher molecular weight products of the condensation reaction such as bis(hydroxyaryl)-diene compounds and resins. This type of condensation product can be completely devoid of the aryloxy-non-conjugated-diene compound. Typically, the amount of aryloxy-non-conjugated-diene compound in the condensation product of the Group C product will vary from about 0.25% up to about 2% by weight of the condensation product and preferably from about 0.25 to 1.5% by weight of the condensation product. The Group C product is generally in the form of a solid.

The Group C product can be prepared by (a) reacting a non-conjugated diene with a hydroxyaryl at a mole ratio of about 0.2 to about 0.5 moles of the diene for each mole of the hydroxyaryl at a temperature of about 130° C. to about 190° C. (b) said reaction conducted in the presence of about 0.03% to about 0.1% of triflic acid based on the weight of hydroxyaryl and about 0.03 to about 0.3 of N-methyl pyrrolidone based on the weight of hydroxyaryl. Lower ratios of pyrrolidone to triflic acid generally require lower reaction temperatures.

Advantages or properties of condensation products produced by this invention include: a large percentage of product can be in the liquid form which can be cured at elevated temperatures with acids and electron beam radiation; the lower viscosity products provide better wetting of aggregates and fibers which in turn provide for better mechanical properties of cured composites; the lower viscosity products also provide for lower viscosity reaction products with materials such as epoxy compounds; the products of this invention cure with little or no release of volatiles such as water or ammonia; and they provide excellent low dielectric constants and low electrical dissipation factors.

The products (condensates) of this invention have many uses. Illustratively they are useful as: hydroxyaryl monomers for the preparation of both epoxy resins and cyanate esters to produce polymers having improved moisture resistance, flexibility and adhesion; a portion of the hydroxyaryl moiety in foundry hydroxyaryl-urethane binders in order to improve aluminum shakeout; epoxy curatives for use in electrical grade laminates where improved moisture resistance is desired; and polymerizable monomers via acid, electron beam or ultraviolet radiation. Due to good heat resistance epoxy resins cured with products of this invention are suitable in micro electronics, especially as encapsulation materials for semi conductors. The monomers and polymers of this invention can also be used in the same manner as other hydroxyaryl/diene monomers and polymers.

The various condensation products of this invention can be used neat or as part of various compositions mentioned above together with conventional solvent, adjuvants, as well as compounds or resins which are reactive and non-reactive. Illustratively, the condensation products of this invention can be used in compositions comprising the product together with: solvents; catalysts; reactive resins such as epoxy, phenolic resole and urethane resins. Typical solvents include ketone, e.g., methyl ethyl ketone, methyl isobutyl ketone, alcohols having from 1 to about 5 carbon atoms, and mono ethers and mono acetates of ethylene, propylene, and diethylene glycols and mixtures thereof. In such solutions, the solids can vary from about 30% to 80% by weight and the solvent can vary from about 20% to about 70%. In such compositions the condensation products of this invention can comprise varying percentages of the composition such as from about 5% to 30% % and preferably from about 10% to 20% by weight of the composition.

In the products and processes of this invention, the diene can be an individual diene or a mixture of dieries and the hydroxyaryl can also be an individual hydroxyaryl or a mixture of hydroxyaryls.

The following examples are illustrative of the invention and its advantageous properties. In the examples as well as elsewhere in this application, all parts and percentages are by weight unless otherwise indicated.

It needs to be pointed out that the molecular weights shown in the examples are far short of the theoretical values. The size exclusion chromatography readings (SEC) of molecular weights used in this case are highly dependant on hydrodynamic volume which causes the discrepancy. Nevertheless, although such molecular weights are well below theoretical and therefore erroneous on an absolute basis, such molecular weights discern differences between higher molecular weight and lower molecular weight materials and can thus be used on a comparative basis.

The weight average molecular weight(Mw) and number average molecular weight (Mn) values obtained by size exclusion chromatography (SEC) reflect the average hydrodynamic volume of the molecules and usually (except for simple hydroxyaryl, phenol, cresol, bisphenol-A and bisphenol-F) do not reflect an accurate molecular weight. For example SEC molecular weight for the following pure materials as shown in Table A below are significantly lower than theoretical. The abbreviation "VPO" in Table A stands for vapor phase osmometry and is more in line with theory as compared to SEC. The VPD was performed in toluene.

TABLE A

| Material | Mw/Mn (theory) | Mw/Mn via SEC | Mn via VPO |
|---|---|---|---|
| Dicyclopentadiene | 132/132 | 89/89 | — |
| d-Limonene | 136/136 | — | 143 |
| 4-Cyclopentyl-phenol | 162/162 | 122/121 | 171 |
| Tetrahydrodicyclopentadiene | 136/136 | 88/88 | — |

It can be seen from Table A that the number average molecular weights via vapor phase osmometry (VPO) is more in line with theory.

The weight average molecular weight (Mw) and number average molecular weight (Mn) herein are measured using size exclusion gel permeation chromatography and phenolic compounds and polystyrene standards. The sample molecular weight to be measured is prepared as follows: the sample is dissolved in tetrahydrofuran and the solution is run through a gel permeation chromatograph. For Examples 1–27 and 1x–8x, the SEC peak at 95±1 was excluded from the calculation of molecular weight. This would exclude phenol and the hydroxyphenyl-non-conjugated-diene compound.

EXAMPLES 1–27

Table 1A below, shows reactants and reaction conditions for Examples (Ex) 1 through 27 whereas Table 1B shows properties of the reaction products for each of the individual examples (Ex). The method for production of the condensates in Examples 2–27 are the same as that for Example 1 given below, except as may be indicated on Table 1A and for a two hour addition of diene instead of one hour.

EXAMPLE 1

A Low Viscosity Phenol/Dicyclopentadiene Condensate

A multi-neck 500 ml flask with stir bar and fitted with a thermometer and condenser was charged under nitrogen with: 150 g (grams) of phenol (1.59 moles); 5 g of N-methyl pyrrolidone(NMP) (3.33% based on the weight of phenol); and 0.9 g of triflic acid (0.6% based on the weight of phenol). The stirred solution was heated to 95° C. and over the course of 1.5 hours 70 g (0.53 moles) of dicyclopentadiene (Ultrene 97 of B.F. Goodrich Co.) was added at 95° C.±1° C. This provided a diene/phenol mole ratio of 0.33. The reaction mixture, over the course of about ten minutes, was heated to 119° C. and held at 119° C. for one hour. The reaction mixture was then cooled slightly and 100 ml (milliliters) of warm water was added and stirred well. Upon standing, about 88 ml clear aqueous layer was removed and the organic layer returned to the reaction flask for distillation. After 62 g of atmospheric distillate was collected, vacuum distillation was continued over about 45 minutes with final temperature of 153° C. at slightly less than 30 inches vacuum. Yield of the dark amber liquid was 115 g, vacuum distillate was 99 g and contained 90.5% phenol and 6.8% water. Twenty grams of the dicyclopentadiene/phenol condensate was dissolved in 20 g of toluene and 15 g of n-heptane and extracted with 40 g water. The organic layer was evaporated at ambient temperature to about 22 g and then dried at 125° C. to 130° C. to give 19.3 g liquid with a viscosity of 340 centistokes (about 400 cps).

A solid could be isolated from the original 115 g by adding slightly to less than equal weight of n-heptane, cooling to about −10° C. and quickly suction filtering, rinsing with pre-cooled n-heptane and vacuum drying. Molecular weight of the liquid and solid products were (Mw/Mn) 170/152 and 166/155, respectively.

Definitions or explanations for abbreviations, headings and subscripts shown in Table 1A and 1B below as well as in examples and other tables herein are as follows unless the context indicates otherwise:

"Ex." means an example such as for the example numbers;

"Diene" such as used in headings refers to the specific diene employed in the example involved wherein: "D-97" is dicyclopentadiene (Ultrene 97 of BF Goodrich of Akron, Ohio), "D-99" is dicyclopentadiene (Ultrene 99 of BF Goodrich), "L-99" is D-limonene (Limonene HP of T2 Labs of Jacksonville, Fla.) wherein the "99" indicates 99% purity;

the "Triflic Acid Cat. %" heading is the percent of trifluoromethanesulfonic acid, by weight, based on the weight of phenol in the reaction mixture of the example involved:

NMP is N-methyl pyrrolidone; NC$_6$P is N-cyclohexyl pyrrolidone; MeOH is methanol; H$_2$O is water; and PVP is poly(2-vinyl pyrrolidone);

the "Catalyst Modifier %" heading is the percent of the retarder by weight, based on the weight of phenol in the reaction mixture for the example involved;

the "Mole Ratio is the mole ratio of diene to phenol;

the "Reaction Conditions" heading provides the beginning, "Start" temperature in degrees centigrade"(° C.)"; and the "Final"(° C./hr)" for the Final temperature and time of reaction before neutralization of the trifluoromethanesulfonic acid catalyst and removal of phenol from the reactior mixture;

the "Mw"/Mn" heading refers to weight average molecular weight "(Mw)" over number average molecular weight "Mn";

the "Viscosity cps (° C.)" heading means cps viscosity at the temperature in parenthesis, provided however that in those instances wherein an asterisk "*" occurs in Table 2A, the viscosity is estimated in gardner units at the temperature within the parenthesis;

the "Misc" heading in Table 1 B are observations for the various experiments such as: "solid" to indicate the physical state of the product; "prod" as an abbreviation for product; "purified" to incicate that the product was purified, and "sol in" to indicate that the product was soluble in one of the following solvents, namely, "$C_7H_{16}$" for heptane, IPA for isopropyl alcohol, and MEK for methyl ethyl ketone.

TABLE 1A

DIENE/PHENOL ADDITION PRODUCTS

| Ex. | Diene | Triflic Acid cat. % | Catalyst Modifier % | Mole Ratio | Reaction Conditions Start (° C.) | Final (° C./hr) |
|---|---|---|---|---|---|---|
| 1 | D-97 | 0.6 | 3.33 NMP | 0.33 | 95 | 119/1 |
| 2 | D-97 | 0.6 | 3.33 NMP | 0.33 | 90 | 140/1 |
| 3 | D-97 | 0.16 | 0.5 NMP | 0.23 | 100 | 130/1 |
| 4 | D-97 | 0.16 | 0.5 NMP | 0.23 | 100 | 100/1 |
| 5 | D-97 | 0.16 | None | 0.23 | 100 | 130/1 |
| 6 | D-97 | 0.16 | None | 0.23 | 100 | 100/1 |
| 7 | D-99 | 0.08 | 0.25 NMP | 0.23 | 100 | 130/1 |
| 8 | D-99 | 0.08 | 0.25 NMP | 0.23 | 100 | 100/1 |
| 9 | D-99 | 0.08 | 0.25 PVP | 0.23 | 100 | 130/1 |
| 10 | D-99 | 0.08 | 0.25 PVP | 0.23 | 100 | 100/1 |
| 11 | D-99 | 0.08 | 0.28 $NC_6P$ | 0.23 | 100 | 130/1 |
| 12 | D-99 | 0.08 | 0.25 NMP | 0.23 | 80 | 120/1 |
| 13 | D-99 | 0.08 | 0.25 NMP | 0.23 | 80 | 100/1 |
| 14 | D-97 | 0.1 | 0.05 MeOH | 0.3 | 50 | 50/2.5 |
| 15 | D-97 | 0.1 | 0.05 $H_2O$ | 0.3 | 50 | 50/2.5 |
| 16 | D-99 | 0.05 | 0.05 $H_2O$ | 0.25 | 50 | 70/2 |
| 17 | D-99 | 0.05 | 0.05 $H_2O$ | 0.25 | 50 | 50/2.5 |
| 18 | D-99 | 0.05 | None | 0.2 | 45 | 160/2 |
| 19 | D-99 | 0.05 | None | 0.2 | 45 | 45/2.5 |
| 20 | D-99 | 0.05 | 0.05 NMP | 0.2 | 45 | 175/2 |
| 21 | D-99 | 0.05 | 0.05 NMP | 0.2 | 100 | 175/2 |
| 22 | D-99 | 0.05 | 0.05 NMP | 0.2 | 130 | 130/2 |
| 23 | L-99 | 0.05 | 0.05 NMP | 0.2 | 45 | 75/4 |
| 24 | L-99 | 0.05 | 0.05 NMP | 0.2 | 45 | 45/2.5 |
| 25 | L-99 | 0.05 | 0.05 NMP | 0.2 | 130 | 130/2 |
| 26 | L-99 | 0.05 | 0.05 NMP | 0.2 | 160 | 160/2 |
| 27 | L-99 | 0.05 | None | 0.2 | 130 | 130/2 |

TABLE 1 B

DIENE/PHENOL CONDENSATION PRODUCT PROPERTIES

| Ex. | Mw/Mn | Viscosity cps (° C.) | Misc. |
|---|---|---|---|
| 1 | 166/155 | | solid |
|   | 170/152 | 340(25)* | purified liquid |
| 2 | 283/187 | 113(100) | — |
| 3 | 226/179 | 100(100) | — |
| 4 | — | 589(25)* | sol in $C_7H_{16}$ |
| 5 | 582/334 | 3060(125) | solid prod |
| 6 | 535/310 | 1440(125) | solid prod |
| 7 | 212/164 | 75(100) | sol in MEK |
| 8 | 151/132 | 550(25)* | sol in $C_7H_{16}$ |
| 9 | 213/173 | 60(100) | — |
| 10 | 155/145 | 1760(25)* | sol in $C_7H_{16}$ |
| 11 | 230/171 | 90(100) | sol in MEk |
| 12 | 202/165 | 40(100) | — |
| 13 | 188/150 | 250(25)* | sol in $C_7H_{16}$ |
| 14 | 180/157 | 25(100) | — |
| 15 | 153/143 | 500(25)* | Sol in $C_7H_{16}$ |
| 16 | 217/176 | 100(100) | — |
| 17 | 175/154 | 58(100) | Sol in IPA |
| 18 | 392/277 | 760(125) | solid prod |
| 19 | 189/163 | 25(100) | — |
| 20 | 447/305 | 4453(125) | solid prod |
| 21 | 395/268 | 425(150) 330(125) 85(150) | solid prod |
| 22 | 247/187 | 135(100) | — |
| 23 | 253/213 | 255(125) | solid prod |
| 24 | 188/169 | 30(100) 620(65) | — |
| 25 | 233/198 | 375(125) | solid prod |
| 26 | 205/177 | 100(125) | solid prod |
| 27 | 238/210 | 272(125) | solid prod |

*Gardner tube viscosity.

(A) From the above Tables 1A and 1B it can be seen that the weight average molecular weights (Mw) vary from 151 to 582 which reflects the transition from mobile liquids to solids. This can be specifically seen from the following Table 1C

TABLE 1C

| Property | Range | Ex's |
|---|---|---|
| Molecular weight, Mw | 151–582 | 8, 5 |
| Viscosity, cps | 250 (25° C.)–4453 (125° C.) | 13, 20 |

(B) An increase in diene feed temperature reduces molecular weight and viscosity (EX.'s 20 vs. 21).
(C) An increase in post feed temperature increases molecular weight and viscosity (Ex.'s 5 vs. 6, 7 vs. 8, 16vs 17 and 18 vs 19)
(D) Replacement of NMP by poly(2-vinyl pyrrolidone) (PV) is interesting in that at the higher post feed temperature (130°) viscosity decreased (Ex.'s 9 vs. 7) whereas at lower temperature (100° C.) the viscosity more than doubled (EX.'s 10 vs. 8).
(E) Doubling both catalyst and NMP had little effect on molecular weight and viscosity (Ex's 3, 4 vs. 7, 8).
(F) Limonene based resins vary in color from pale yellow to light amber whereas dicyclopentadiene (DCPD) resins are generally darker.
(G) Replacement of methanol by water (Ex15 vs 14) led to a decrease in molecular weight and viscosity. This may be attributable to the fact that water at equal weight to methanol provides more retarder equivalents.
(H) Absence of a retarder significantly increases molecular weight and viscosity, see Examples 3, 4 and 25 versus (vs) 5, 6 and 27.

TABLE 2A AND 2B

The examples in these two tables were run in the same manner as Example 1 hereinabove and the various notes and abbreviations in Table1A and 1B apply herein unless otherwise indicated. Table 2A shows monomers and reaction conditions and Table 2B shows properties of the condensates. Each of the example (Ex) numbers of these tables has the suffix "X" so as to distinguish them from other examples in this case. In addition to the notes and abbreviations which apply from Tables 1A and 1B, the term "ETNB" refers to 5-ethylidene-2-norbornene; "*" indicates food grade limonene of 96% purity; and "m.p." refers to the melting point of the product.

TABLE 2A

| Ex. | Diene | Triflic Acid cat. % | Catalyst Modifier % | Mole Ratio | Reaction Conditions Start (° C.) | Final (° C./hr) |
|---|---|---|---|---|---|---|
| 1X | D-99 | 0.05 | 0.05 NMP | 0.20 | 100 | 175/2 |
| 2X | D-99 | 0.05 | 0.05 NMP | 0.20 | 100 | 160/3.25 and 165/.25 |
| 3X | D-99 | 0.05 | 0.05 NMP | 0.20 | 100 | 150/2 |
| 4X | L-96* | 0.05 | 0.05 NMP | 0.20 | 45 | 45/2.5 |
| 5X | L-99 | 0.05 | 0.05 NMP | 0.50 | 45 | 45/5.5 |
| 6X | L-99 | 0.05 | 0.05 NMP | 0.20 | 130 | 130/2.5 |
| 7X | ETNB | 0.08 | 0.25 NMP | 0.20 | 100 | 100/4 |
| 8X | ETNB | 0.05 | 0.15 NMP | 0.20 | 80 | 80/6 and 100/2 |

TABLE 2B

DIENE/PHENOL ADDITION PRODUCT PROPERTIES

| Ex. | Mw//Mn | Viscosity cps (° C.) | Misc. |
|---|---|---|---|
| 1X | 474/300 | — | m.p. 98.8° C. |
| 2X | 371/235 | 223 (125) | m.p. 66.7° C. |
| 3X | 243/188 | — | — |
| 4X | 191/170 | 1713 (65) 45 (100) | — |
| 5X | 265/200 | 630 (100) | — |
| 6X | 236/211 | 375 (125) | m.p. 79° C. |
| 7X | 298/210 | 115 (100) | — |
| 8X | 261/199 | 650 (100) | — |

From the above Table 2B, it can be seen that: high post feed temperatures lead to higher molecular weigh and higher m.p. (melting point) products, e.g., see Example 1X versus Examples 2X and 3X.

EXAMPLE 28
Solid Dicyclopentadiene/Phenol Condensate

A 2 liter 4-neck flask fitted with condenser, overhead stirrer and thermometer was charged with: 975.6 g of phenol (containing 0.05% water); 0.51 g triflic acid, 0.51 g of NMP and under nitrogen blanket was heated to 100° C. A solution of 285.3 g dicyclopentadiene (2.2 moles) (Ultrene 99) and 45 g phenol (total phenol is 1020.6 g or 10.85 moles) was added over 2 hours at 100° C.±0.5° C. This provided a diene/phenol mole ratio of 0.20. The reaction mixture was heated to 160° C. and maintained at 160°±1° C. for 4.5 hours, quickly cooled to 130° C. and then catalyst neutralized with dilute sodium hydroxide to a solution pH of 5.8 (2.5g solution diluted with 25 ml methanol). 691 g phenol was recovered by vacuum distillation with a final temperature of 175° C. under 29.5 inches vacuum. The reaction mixture was then steam sparged at about 150° C. under 20 inches vacuum by slowly introducing 100 ml water over 50 minutes. Product was dried by heating at 160° C. under 29.5 inches of vacuum for 10 minutes and then discharged. Yield was 530 g. This solid product was characterized as follows: phenol of 0.06%; dicyclopentadiene of less than 0.01%; Mw/Mn of 406/246; and viscosity of 299 cps (125° C.:).

EXAMPLE 29
Low Viscosity Dicyclopentadiene/Phenol Condensate

A multi-neck 5 liter flask fitted with condenser, overhead stirrer and thermometer was charged with: 2858 g of phenol (containing 0.03% water); 2.4 g triflic acid; and 7.2 g NMP and under nitrogen blanket was heated to 100° C. A solution of 912 g dicyclopentadiene (6.89 moles, Ultrene 99) and 45 g phenol (total phenol is 2903 g) was added over 2 hours at 100° C.±0.5%. The dicyclopentadiene to phenol mole ratio charged in this example is 0.22. After 65 minutes at 100° C. catalyst was neutralized with a dilute solution of sodium hydroxide to a solution pH of 5.6 (2.5 g solution with 25 ml methanol). Phenol (2270 g) and product (1457 g) were recovered as in the following Example 30 using steam sparging with 200 ml water over 1.25 hours. Product was characterized as follows: phenol 0.24%; Mw/Mn 172/149, does not include the SEC peak at 95±1 (Mw/Mn of 131/115 includes the SEC peak at 95±1); viscosity of 550 cps; refractive index of 1.5711 (25.4° C.).

EXAMPLE 30

Medium Viscosity Liquid Dicyclopentadiene/Phenol Condensate

A multi-neck 5 liter flask fitted with condenser, overhead stirrer and thermometer was charged with: 2903 g phenol (containing 0.03% water) (30.85 moles); 2.39 g of triflic acid; 7.19 g of NMP and under nitrogen blanket was heated to 90° C. 942.4 g of dicyclopentadiene (6.90 moles, Ultrene 97) was added over 2 hours at 90° C.±0.5° C. The dicyclopentadiene/phenol mole ratio was 0.22. After 53 minutes at 90° C. catalyst was neutralized with dilute sodium hydroxide to a solution pH of 5.5 (2.5 g solution with 25 ml methanol). The reaction mixture was set for vacuum distillation at 26.5 inches of vacuum and the temperature set for 130° C. 2303 g phenol was recovered by vacuum distillation with a final temperature of 160° C. under 30 inches of vacuum. The reaction mixture was then steam sparged at about 150° C. under 20 inches vacuum by introducing 150 ml. water over 45 minutes. Product was dried by increasing vacuum to 30 inches. Yield was 1400 g and was characterized as follows: phenol 0.35%; Mw/Mn of 321/190 without the SEC peak at 95±1 (239/140 with the SEC peak at 95±1) viscosity of 2835 cps (25° C.); and the final pH of 2.60 even though neutralization was attempted.

EXAMPLE 31

Effect of Additives on Dicyclopentadiene-Phenol Reaction at 45° C. and Mole Ratio of 0.45

A multi-neck 1 liter flask to be fitted with condenser, overhead stirrer and thermometer was charged with: 414 g of phenol (4.4 moles which contained 0.04% water); 2.08 g of 10% triflic acid in phenol; and 0.2g of N-methyl pyrrolidone. This reaction mixture was heated to 45° C. at which time 262 g of dicyclopentadiene (1.98 moles of Ultrene 97) was added over 2 hours while maintaining 45° C.±0.5° C. The reaction was maintained at 45° C. for an additional 4 hours whereupon catalyst was neutralized by addition of 0.50 g of 10% sodium hydroxide in water. The reaction was heated under vacuum to recover the majority of unreacted phenol at 125–130° C. under 26.5 to 29.5 inches vacuum. Further recovery was obtained by heating at 160° C. under 29.5 inches vacuum. Phenol level was further reduced by introduction of water at 155–160° C. under 20 inches of vacuum and then heating continued briefly at 160° C. under 29.5 inches vacuum. Yield of phenol vacuum distillate was 317 g and yield of condensate was 330 g which was characterized as follows; 0.05% free phenol, Mw/Mn=140/138(112/106 with the SEC peak at 95±1); 0.54% of dicyclopentadiene; viscosity of 270 cps (25° C.) and there was extensive crystallization of the condensate upon standing. The high level of dicyclopentadiene is atypical since levels ore generally below 0.1% which is indicative of quantitative conversion.

Fractionation of Product from Example 31

A solution of 100 g of product from Example 31 and 40 g of n-heptane was extracted with 200 g of 15% sodium hydroxide in water. The resulting mixture was transferred to a separatory funnel and upon standing separated into three layers. The bottom layer was drawn off, cooled, and acidified with concentrated HCl to precipitate about 2 g of gummy material. Acidification of the middle layer precipitated a dark gum which after vacuum drying at 80–90° C. weighed 15 g (phenolic fraction). The organic (upper) layer was washed with 50 ml water and dried, and then vacuum dried as above to give 78 g of light yellow liquid having a viscosity of 127 cps (25° C.) (neutral fraction of phenoxy-dicyclopentadiene which upon standing crystallized). The dark gum had a Mw/Mn of 155/133 with a predominant SEC peak at 131 and a minor peak at 95. The yellow liquid had a Mw/Mr of 103/103 with a major SEC peak at 95 and a minor peak at 131.

EXAMPLES 32–38

In a manner similar to that of Example 31, control runs, i.e., no additive, as well as additives were tested, albeit at different reaction times following addition of dicyclopentadiene. Data as to the reaction conditions are found in Table 32R -38R and the results are found in Table 32S-38S below . For comparative purposes, the data for Example 31 are included in Table 32-38. Examples 32 and 33 were conducted by using twice the amount of reactants, e.g., 8.8 moles of phenol.

TABLE 32R–38R

| Ex | Additive | Time after diene addition, in hours | Solution[f] Refr. Ind. |
|---|---|---|---|
| 31 | N - methyl pyrrolidone | 4 | 1.5560 |
| 32[a] | none | 0.5 | 1.5661 |
| 33[b] | none | 0.5 | 1.5674 |
| 34[c] | N - methyl pyrrolidone | 4.5 | 1.5578 |
| 35 | 2-chloropyridine (pka = 0.49) | 1 at 45° C.* and another 7 at 70° C. | 1.5569 |
| 36 | 2-nitroaniline (pKa = -0.26) | 0.5 | 1.5612 |
| 37 | bis(2-methoxyethyl)ether | 0.5 | 1.5655 |
| 38A | acetanilide (pKa = 0.4) | 0.67 | 1.5609 |
| 38B[d][e] | N - methyl pyrrolidone | 0.5 | 1.5453 |
| 38C[d][j] | N - methyl pyrrolidone | 0.25 | 1.5389 |

*Essentially no reaction occurred after one hour based on refractive index readings.
[a]Reaction exotherm let to significant time at 51° C. during diene addition.
[b]Diene addition made over 3 hours and not 2 hrs.
[c]Diene contained 25.5% trimer and 1.8% tetramer of cyclopentadiene.
[d]d-Limonene (96%) replaced dicyclopentadiene.
[e]Diene addition and post addition at 60° C. prior to catalyst neutralization.
[f]Solution refractive Index (24.5–26.5° C.).
[j]Solution viscosity of 55 (25° C.).

TABLE 32S–38S

| Ex | Yield % | Viscosity, cps (25° C.) | Refr. Index (24.5–26.5° C. | Mn/Mw[i] |
|---|---|---|---|---|
| 31 | 48 | 270[g] | 1.5679 | 140/138 (112/106) |
| 32 | 63 | 7,000 | 1.5779 | 190/159 (149/127) |
| 33 | 62 | 12,300 | 1.5794 | 195/162 (156/131) |
| 34 | 47 | 1,870 | 1.5732 | — (119/110) |
| 35 | 50 | 275[g] | 1.5664 | 143/140 (112/106) |
| 36 | 60 | 383[g] | 1.5689 | 150/143 (116/109) |
| 37 | 57 | 3,675 | 1.5766 | 168/152 (138/123) |
| 38A | 57 | 431[h] | 1.5692 | 159/147 (122/111) |
| 38B[k] | 56 | 5,720(65° C.) | 1.5472 | 217/186 * |
| 38C[j] | 45 | 450(65° C.) | 1.5410 | 193/173 * |

[g]Extensive crystallization upon standing at room temperature.
[h]Slight crystallization upon standing at room temperature.
[i]Values in parentheses include the phenoxy-dicyclopentadiene compound and a trace of phenol.
[k]Ratio of 1:1 molar diene-phenol compounds to bis-(hydroxyaryl)-diene compounds is about 11.1:6.8.
[j]Ratio of 1:1 molar diene-phenol compounds to bis(hydroxyaryl)-diene compounds is about 14.0:6.8
*Indicates that there was no SEC peak at 95 ± 1.

It can be seen from the above Table 32S-38S, that the absence of a retarder as in EX 32 and 33 under very mild conditions, e.g., 45° C. and short reaction times results in high viscosity products. The structure and pKa of additives have a profound effect on reactivity and product viscosity. Nitrogen free bis(2-methoxyethyl)ether (EX 37) gives the highest viscosity of the various retarder additives and 2-chloropyridine (EX 35) shows the slowest reaction at 45° C. Raising addition and post addition temperatures significantly raises product viscosity using d-limonene (EX 38B versus EX 38C). Molecular weight (Mw/Mn) poorly correlates with viscosity.

Fractionation of Product From Example 35 and Isolation of Phenoxy-Exo-Dicyclopentadiene (III)

A solution of 50 g of product from Example 35 in 20 g of n-heptane was extracted with 100 g of 15% sodium hydroxide in water. The organic layer was washed with water and after air drying and then further dried at 80° C. under 28 inches of vacuum to give 37 g of light yellow, very fluid, liquid which largely crystallized upon standing. The aqueous caustic layer was acidified with concentrated HCl to give a dark gum which was washed with water and then vacuum dried to give 11 g of a very dark gum.

Recrystallization of Product From Example 35

Fifty g of extensively crystallized product from Example 35 was dissolved in 150 ml warm methanol and gradually cooled. The slurry was decanted from a small amount of slightly gummy, light tan mass, than cooled in ice water and filtered. The filter cake was then rinsed with 50 ml cold methanol and vacuum dried. Yield of white solid was 15.5 g with a melting point of 60° C. to 65° C. Further recrystallization gave 12 g of phenoxy-dicyclopentadiene compound having a melting point of 65° C. to 67° C. This product is referred to as phenoxy-dihydro-exo-dicyclopentadiene by H. A. Bruson, et al, J. Amer. Chem. Soc. 68, (8/1946) showing a melting point of 70° C. -71 ° C. and a melting point of 66° C. to 67° in Neftekhimiya, 1974, Volume XIV, No. 2, 280–283. The crystalline solid had a Mw/Mn of 99/97 (SE C peak at 96).

EXAMPLE 39

Bisphenol-A/d-Limonene Condensate

A 250 ml flask with stir bar was charged with: 57 g of bisphenol-A (0.25 mole=0.50 equivalents) and 56 g (65 ml) of xylene. This was heated to 105° C. and there was then added 0.5 g of 50% triflic acid in water. Then 41 ml (34.4 g) d-limonene (99%) was added over 25 minutes at 105° C.±2° C. The reaction temperature was allowed to drop to 90° C. over 35 minutes at which time it was raised to 105° C. and an additional 40 ml of d-limonene (total of 68 g, 0.5 mols) was added over 45 minutes. After 1.5 hours at 105° C. catalyst was neutralized with 0.5 g of 15% sodium hydroxide in water. The well stirred reaction mixture was then allowed to stand overnite at room temperature. Then 176 g of liquor was separated from solid (salt), xylene, and unreacted d-limonene removed by vacuum distillation to 166° C. at 30 inches of vacuum. Yield of product and distillate was 111 g and 63 g respectively. Product was characterized by 3.8% free bisphenol-A; Mw/Mn of 310/235; and viscosity of 1250 cps (100° C.).

EXAMPLE 39A

This example is run in a manner similar to Example 39 but by replacing d-limonene with 16.5 g (0.125 moles) of dicyclopentadiene (Ultrene 99) and using 0.06 g of triflic acid, instead of 0.5 g of 50% triflic acid in water, and 0.12 g of N-methyl pyrrolidone. Product, after neutralization of catalyst and removal of solvent and a majority of unreacted bisphenol-A can be obtained which is predominantly the condensate of 2 moles of diene with one mole of bisphenol-A in which the ratio of aryloxy- to hydroxyaryl-content is about 3:2.

EXAMPLES 40–45

Effect of Post Feed Temperatures and Time

Table 40A-45A shows the reaction conditions as well as the solution viscosity of Examples (EX) 40–45 whereas Table 40B-45B illustrates the effect of time and temperature of condensates prepared by Examples 40–45 of this invention after a 2 hour feed of dicyclopentadiene, at room temperature, to a reaction vessel containing a mixture of phenol, triflic acid and N-methyl pyrrolidone (NMP) preheated to a temperature of 60° C. and a 2 hour hold at 60° C. after completion of the diene feed. The diene to phenol mole ratio for each example was 0.45 and the quantity of each of triflic acid and the NMP was 0.05% based on the weight of phenol. All of the following examples, except Example 40, show more than one Time/Temp. reading. The reason for this is that the reaction mixture was heated for a time at a certain temperature, and then heating was continued for an additional time at another temperature. Thus, the time of reaction is additive, e.g., in EX 45 in the table it shows that the reaction mixture was heated first for 4 hours and subsequently for 3 hours at a higher temperature. The total time of heating in the table for EX 45 is 7 hours and this is in addition to the two hour feed time and the two hour hold time used for each example. Table 40A-45A shows the time period heal: was applied, after the initial 2 hour feed and the 2 hour hold at 60° C., the temperature of heating as well as the refractive index (Refr. Ind.) and viscosity (Visc) of the reaction mixture as explained in the superscripts of Table 40A-45A. The yield, refractive index (Refr. Ind.), viscosities (Vis), and Mw/Mn in Table 40B-45B are those of the condensate product after all the time and heating cycles.

TABLE 40A–45A

Reaction Conditions of Post Feed Temperatures and Time Study

| EX | Time (hours)[a] | Temperature (° C.)[a] | Solution[b] Refr. Ind. | Visc. |
|---|---|---|---|---|
| 40 | 2 and ⅓ | 90 | 1.5620 | 67.6 |
| 41 | 3 and ¼ | 90 | 1.5619 | 68.6 |
| 42 | 1 and ⅙ | 80 | — | — |
|  | 1 and ½ | 100 | 1.5636 | — |
| 43[f] | 2 | 60 | — | — |
|  | 2.25 | 100 | 1.5652 | 111 |
| 44 | 2 | 140[d] | — | — |
|  | 2 | 160[e] | — | 672 |
|  | 5 | 180 | — | 29,500 |
| 45 | 4 | 115–160 | — | 268 |
|  | 3 | 170 | — | 5160 |

[a]After 2 hour diene feed at 60° C. and 2 hour hold at 60° C.
[b]Refractive Index (Refr. Ind.) (24.5–26.5° C.) and viscosity (visc) (25° C.) of reaction solution.
[d]Mw/Mn = 270/186 (160/118)
[e]Mw/Mn = 333/209 (219/130)
[f]Two hours at 60° C. after diene addition, the dicyclopentadiene content was 1.73% which represents 95.5% conversion.
For [d] and [e] above, the values in parentheses include the SEC peak at 95 ± 1.

TABLE 40B–45B

Condensate Properties

| Ex | Yield, %[c] | Refr. Ind. | Viscosity, cps (25° C.) | Mw/Mn[d] |
|---|---|---|---|---|
| 40 | 62 | 1.5714 | 767 | 157/146 — |
| 41 | 61 | 1.5717 | 908 | 156/146 — |
| 42 | 56 | 1.5751 | 2580 | 170/150 (143/122) |
| 43 | — | 1.5767 | 4,480 | 175/152 (149/125) |
| 44 | 61 | Solid | 520 (125° C.) | 642/286 [e] |
| 45 | 64 | Solid | 156 (125° C.) | 473/241 [e] |

[c]Based on % of phenol and diene, by weight charged to the reaction.
[d]Values in parentheses include the phenoxy-dicyclopentadiene compound and a trace of phenol.
[e] Does not contain an SEC peak at 95 ± 1.

In a manner similar to Example 40 above other non-conjugated dienes and phenols can be used in place of the diene and phenol used in Example 40. Also, mixtures of reactant monomers, including conjugated dienes, can be used such as: 10 mole % of diene can be replaced by 2,5-dimethyl-2,4-hexadiene, a conjugated diene; 20 mole % of phenol can be replaced by m-cresol; and 10% of phenol can be replaced by resorcinol. However, with resorcinol which is a solid (melting point of about 111° C.) one would need to use an inert solvent such as toluene, xylene, chlorobenzene, or a lower reactive, removable phenolic such as ortho cresol to at least partially dissolve the very reactive resorcinol and the reaction conditions would be relatively mild, e.g., temperatures of about 60° C., at least initially.

EXAMPLE 40A

In a manner similar to Example 40 but replacing phenol by 50% of the equimolar amount of resorcinol, using twice the weight of resorcinol by 1:1, by weight, ortho-xylene/ortho-cresol as solvent, neutralizing catalyst, removing solvent and any unreacted resorcinol, a product can be obtained which has approximately equal amounts of aryloxy and hydroxyaryl groups.

EXAMPLE 42A

In a manner similar to Example 42, but by replacing phenol with an equimolar amount of meta-cresol, approximately equal amounts of aryloxy-dicyclopentadiene compound and hydroxyaryl-dicyclopentadiene compound can be obtained.

The following shows the procedure and results for the isolation of phenol-dicyclopentadiene product. One hundred g of product equivalent to that of Example 40 was dissolved in 150 ml of n-hexane and extracted with a solution of 100 ml methanol and 30 ml of water. The methanol-water phase was evaporated and vacuum dried at 60° C. to give 2.9 g of dark amber, viscous liquid. Hexane was removed to give 95 g of amber syrup which after cooling was extracted with 200 g of ice cold 10% sodium hydroxide in water. The aqueous extract was washed with 50 ml of n-heptane and then precipitated by gradual addition to stirred ice cold 50 g concentrated HCL. The precipitated oil was extracted with 70 ml of n-hexane and this solution was washed with 50 ml water. Hexane was evaporated and residue dried at 60–100° C. at 28.5 to 29 inches of vacuum for 3 hours. Yield of amber syrup was 30 g and was characterized as follows: % OH of 7% (theory is 7.5%) Mw/Mn of 176/143 (includes SEC peak at 96) and it was noticed that only one significant peak was present at 132 whereas the theoretical for the phenol-dicyclopentadiene compound is 226; viscosity of 20,600 cps (25° C.) wherein 66.8% by weight of this syrup is the phenol-dicyclopentadiene compound; 11.4% is the phenoxy-dicyclopentadiene compound (SEC peak at 96); and 21.8% is that of higher molecular weight compounds (SEC peak at 233).

One gram (g) of the dicyclopentadiene/phenol resin of Example 45 above was exhaustively extracted with 5.0 g of n-heptane, evaporated and vacuum dried to give 0.34 g (34%) of a tacky resin. In contrast product from Example 50 is essentially insoluble in heptane.

EXAMPLE 46

Dicyclopentadiene/d-Limonene/ Phenol Condensate

A one liter multi-neck flask to be fitted with overhead stirrer, thermometer, condenser, and addition funnel was charged with: 580 g, phenol (6.16moles containing 0.04% water); 0.48 gm triflic acid; and 1.44 g N-methyl pyrrolidone and heated under nitrogen to 100° C. A solution of 94.0 g of d-limonene (HP, 0.69 mole) and 91.2 g of dicyclopentadiene (Ultrene 99, 0.69 mole) was then added over 2 hours to the phenol plus the catalyst system which was at 100° C.±1° C. . The reaction solution was further heated at 100° C. for 2 hours whereupon catalyst was neutralized with 0.85 g of 15% sodium hydroxide in water. Phenol was then removed by vacuum distillation as in Example 31 followed by steam sparging with 150 ml water at 155–160° C. under 20 inches of vacuum. Product was dried at 160° C. under 30 inches of vacuum . Yield of dark amber gum was 295 g and vacuum distillate was 437 g. Product was characterized as follows: phenol of less than 0.05%; Mw/Mn=237/200 (204/159 including SEC peak at 95±1); viscosity, 250 cps (100° C.) and 1500 cps (70° C.).

EXAMPLE 47

The procedure of Example 31 was followed but using 8.8 moles of phenol and a mole ratio of 0.5 of the diene to the phenol and a diene addition time of 3.25 hours while maintaining 45° C.±0.50° C. The reaction was maintained at 45° C. for 71 minutes whereupon catalyst was neutralized to a pH of 5.24. Phenol was recovered in a manner similar to Example 31. Yield of product was 829 g which was characterized as follows: 1.43% of free phenol; Mw/Mn=519/244; <0.1% of dicyclopentadiene; viscosity of 108,200 cps at 25° C. (8,800 cps at 40° C.). Product was almost completely soluble in warm n-heptane, not completely soluble in methanol (approximately 24% insoluble using 2.0 g of product with 20 g methanol); pH of 2.08 when 2.5 g of product was used in 25 ml of methanol.

Two grams of the dicyclopentadiene/phenol resin of the above Example 47 was stirred overnight with 20 g of methanol. Clean liquor was separated from dark solid which after drying weighted 0.47 g (24%). This material was insoluble in 10% aqueous sodium hydroxide. The methanol and caustic insolubility indicate an essentially non-phenolic material.

EXAMPLE 48

The formulation and mole ratio of Examples 40–45 was followed using 8.8 moles phenol but adding the dicyclopentadiene at 160° C. instead of 60° C. over 2⅙ hours and further heating at 160° C. for one hour before raising the temperature to 180° C. (±1° C.) and maintaining it for 8 hours. Solution viscosity at that point of time was 8,490 cps (25° C.). Reaction was cooled to 130° C. and catalyst neutralized to pH of 7.48 using 1.2 g of 10% sodium hydroxide solution in water. Phenol was recovered by heating to 180° C. at 29 inches of vacuum and steam sparging at this temperature at 20 inches of vacuum. Yield of product (not corrected for extensive sampling) was 873 g which was characterized as follows less than 0.1% free phenol; viscosity of 286 cps at 125° C.; Mw/Mn=686/285. SEC areas show the following composition: 1.6% phenoxy-dicyclopentadiene compound; 18.2% of hydroxyphenyl-dicyclopentadiene compound; 21.7% of bis(hydroxyphenyl)-dicyclopentadiene compounds; and 58.5% of higher molecular weight materials.

EXAMPLE 48A

In a manner similar to Example 48 but by replacing phenol by an equimolar amount of m-cresol and adding dicyclopentadiene at 140° C., product can be obtained with contains less than 2%, of hydroxyaryl-dicyclopentadiene compound.

EXAMPLE 49

Dicyclopentadiene/Phenol Condensate With High Diphenolics and No 1:1 Molar Compounds, All Without Use of Retarder.

To a mixture of 3,407 g (36.2 moles) phenol (containing 0.05% water) and 3.41 g of triflic acid under nitrogen, there was added over a two hour period 430 g of dicyclopentadiene (3.25 moles) (Ultrene 97) at 75–78° C. This provided a diene/phenol mole ratio of 0.090. The eaction mixture was then heated to 100° C. and maintained at this temperature for 3 hours whereupon catalyst was neutralized to a pH of 5.0 by addition of 3.49 g of 20% sodium hydroxide solution in water. Phenol was recovered by distillation up to 165° C. and 26.5 inches of vacuum and by sparging with 150 ml water under these conditions. Yield of product was 1,005 g which was characterized as follows:

<0.05% free phenol; Mw/Mn=312/257; viscosity of 1,026 cps (125° C.) . Integrated area of diphenolics from SEC profile was about 75%.

Essentially, pure diphenolics isomers was isolated by extracting 70 g product with 300 ml of n-heptane at boiling point, decanting off the colorless hot liquor and removing heptane. The off-white solid was soluble in a 10% solution of sodium hydroxide in water, had a Mw/Mn=256/252 and the % of hydroxyl was 10.5% whereas theoretical is 10.6 and hydroxyl equivalent was found to be 162, whereas the theoretical is 160.

Percent dicyclopentadiene was determined in many phenolic distillates. Dicyclopentadiene was not detected (i.e., it was less than 0.1%) in the product of Examples 32, 33, 35, 36, 37, 40, 43, 44, and 45. However, 0.54% was detected in the distillate of Example 31. This corresponds to about 6.5% of the dicyclopentadiene initially charged. However, even when a significant amount of the diene was detected in the vacuum distillate, none was detected in the condensation product.

Properties of Condensates Obtained by Size Exclusion Chromatography (SEC)

Profiles of condensates obtained by size exclusion chromatography (SEC) were integrated by areas. The aryloxy-non-conjugated-diene compound, i.e., neutral or ether compound, shows an SEC peak at 95±1 whereas the hydroxyaryl-non-conjugated diene compounds show a peak at 133±1. The results are shown in Table D below. In Table D, the entries under EX. is the example number of examples hereinabove set forth and fractions or extracts of such examples wherein: the letter "A" is the recrystallized solid from Example 35; the letter "B" is fraction 1 of Example 33; the letter "C" is fraction 3 from Example 33; the letter "D" is the liquid fraction from Example 35; the letter "E" is the gum fraction from Example 35; and the letter "F" is the heptane extracted bis(hydroxyaryl)-diene compound from Example 49. The column heading "1:1 ether %" is the amount of the aryloxy-non-conjugated-diene compound. The column heading "1:1 phenolic %" is the amount of the hydroxyaryl-non-conjugated-diene compound wherein the bonding of the hydroxyaryl and the non-conjugated diene is through a carbon to carbon bond. The "III/IV ratio" is the ratio of the aryloxy-non-conjugated-diene to hydroxyaryl-non-conjugated-diene compound. The column heading of "% of hydroxyl and (hydroxyl equivalent" is self explanatory. The column heading "Viscosity" is in cps at 25° C. unless otherwise indicated such as when the product is solid, in which case "m. p." indicates the melting point at a specified temperature.

TABLE D

Properties of Condensates Obtained by
Size Exclusion Chromatography (SEC)

| (EX) | 1:1 Ether, % | 1:1 Phenolic, % | III/IV Ratio | % OH[a] and (hydroxyl equivalent) | Viscosity |
|---|---|---|---|---|---|
| A[b] | 97.5 | 2.5 | 39 | 0.5(3,400) | m.p. 65–67° C. |
| B | 59.2 | 17.2 | 3.44 | 2.01(845) | — |
| C | 3.6 | 58.6 | 0.06 | 7.26(234) | — |
| D | 82.9 | 15.8 | 5.2 | — | — |
| E | 19.7 | 72.2 | 0.27 | — | — |
| 40 | 54.1 | 37.9 | 1.4 | 2.21(770) | 767 |
| 38A | 60.5 | 33.0 | 1.83 | — | 431 |
| 42 | 41.6 | 42.2 | 0.99 | — | 2580 |
| 43 | 38.2 | 43.5 | 0.88 | 2.57(662) | 4480 |
| 33 | 33.0 | 40.5 | 0.81 | 2.93(579) | 12300 |
| 47 | — | — | — | — | 108,200 |
| 36 | — | — | — | — | 383 |
| 45 | 0.4 | 24.5 | 0.02 | — | 156(125° C.) |
| 44 | 0 | 16.3 | 0 | 7.39(230) | 520(125° C.) |
| 31 | 68.7 | 31.3 | 2.19 | — | 270 |
| F | 0 | 0 | — | 10.5 | Solid at 25° C. |

[a]The calculated % of OH: for the bis(hydroxyaryl)-non-conjugated diene is 10.6; for the aryloxy-non-conjugated-diene compound is 0.0 and hydroxyaryl-non-conjugated-diene compounds is 7.5; and for the polycondensate is 7.5. The polycondensate is a chain of self polymerized units and polymerized mixture of units.
[b]Contains traces of methanol and hydroxyphenyl-dicyclopentadiene compound.

A determination of the hydroxyl number (and equivalent) is made as follows: A solution of 2.0 g sample is refluxed for 2 hours with 25 ml of pyridine/acetic anhydride solution (from 250 ml pyridine plus 60 ml of the anhydride). The reflux condenser is rinsed with 5 ml water and the contents heated for an additional 5 minutes. Heat is removed and the condenser rinsed with 25 ml methanol. After cooling to room temperature, the contents are titrated with 1.0 N sodium hydroxide to pH of 9 by using the pH meter. The titre is expressed as "A". For the blank ("B"), a mixture of the same volume of acetic anhydride, pyridine and water as used above is mixed and allowed to stand for 15 minutes shortly before titration, the same amount of methanol as was used above as a rinse is added. "B" is expressed in mls (milliliters). The calculation for "%OH" is:

$(B-A)(1N)(0.017)(100)$ divided by Sample Weight, in grams.

The calculation for hydroxyl equivalent is:

17×100 divided by %OH.

COMPARATIVE EXAMPLE 50

Preparation of Dicycloperitadiene/Phenol Resin Using Boron Trifluoride Catalyst and at a Mole Ratio of 0.077 of Dicyclopentadiene to Phenol Example 1 of U.S. Pat. No. 4,927,905 was essentially followed but at a mole ratio of 0.077 of dicyclopentadiene to phenol. Thus, dicyclopentadiene (132 g., 1.0 mole) was added over one hour under nitrogen blanket to a solution of phenol (1,223.3 g ,13 moles) and boron trifluoride etherate (6.8 g, 0.5% on phenol) at 70° C. The reaction was then heated over 4 hours to 150° C. and maintained at this temperature for 1.5 hours. Reaction was then cooled to 60° C. and catalyst neutralized with 6.5 g of 45% KOH. Phenol was recovered by vacuum distillation to 190° C. at 26 inches of vacuum and then the residue steam sparged with 100 ml water at 185–190° C. under 26 inches of vacuum. Product (312 g) was characterized as follows: viscosity of 1210 cps at 125° C. Mw/Mn 322/262; phenol of <0.05%; boron of 0.027%; fluorine of 1.06%; phenol-dicyclopentadiene compound of trace (<1%). Also no phenoxy-dicyclopentadiene compound (ether) was detected.

COMPARATIVE EXAMPLE 51

Comparative Example for Preparation of Dicyclopentadiene/Phenol Resin Using Boron Trifluoride Catalyst and Mole Ratio of 0.25 of Dicyclopentadiene to Phenol Dicyclopentadiene (198.5 g, 1.5 moles) was added over one hour under nitrogen blanket to a solution of phenol (565 g, 6.0 moles) and boron trifluoride etherate (2.25 g, 0.4% on phenol) at 70° C. Reaction mixture was further heated and phenol and product recovered as in Example 50. Product (317 g) was characterized as follows: viscosity of 20,900 cps at 125° C.; 942 cps at 150° C.; Mw/Mn of 580/318; and phenol-dicyclopentadiene compound of about 3%.

COMPARTIVE EXAMPLE 52

Dicyclopentadiene/Phenol Condensate Using Methanesulfonic Acid Catalyst and Acetanilide Retarder The procedure of Example 38A was followed except that an equimolar amount of methanesulfonic acid(1.3:3g of 10% acid in phenol) replaced 2.08 g of 10% triflic acid in phenol. Essentially, no reaction occurred after one hour at 45° C. after diene addition at 45° C. (refractive index of 1.5314 at 27.7° C.). Very little reaction occurred after another 4 hours at 70° C. when the refractive index was 1.5344 (27.6° C.). This is versus a refractive index of 1.5548 (26.1° C.) for Example 38A at this time and 1.5569 after 7 hours at 70° C. The reaction was then heated to 90° C. wherein the refractive index changed as shown in Table 52 below wherein R. I. is refractive index at 25±0.5° C.

TABLE 52

| Hours at 90° C. | R.I. (25 ± 0.5° C.) |
|---|---|
| 1 | 1.5370 |
| 3 | 1.5404 |
| 5 | 1.5430 |
| 7 | 1.5449 |
| 9 | 1.5473 |
| 11 | 1.5497 |

After 11 hours at 90° C., as shown in Table 52 above, the reaction mixture was neutralized and then analyzed. The analysis showed: 14.9% of unreacted dicyclopentadiene which translates to but a 61% conversion of the diene; and a ratio of about 3.4 of phenoxy-dicyclopentadiene compound to hydroxyphenyl-dicyclopentadiene compound.

From the above Comparative Example 52 and Table 52 it can be seen that the very strong methanesulfonic acid (about 0.5 times the acidity of sulfuric acid and about twice the strength of HCl measured by conductivity in acetic acid at 25° C.) is relatively ineffective in comparison to triflic acid.

EXAMPLE 53

Dicyclopentadiene/Phenol Condensate at Mole Ratio of 0.30

Example 48 was followed using 9.9 moles phenol (instead of 8.8) and 3.0 moles of the diene but after the one hour at 160° C. the reaction was heated 2 hours at 180° C. and 10 hours at 185° C. Solution viscosity was 21,480 cps (25° C.). Catalyst was neutralized with 1.47 g of 10% NaOH solution in water. Phenol was recovered under vacuum at 185° C. and steam sparging at this temperature. Product (755 g) was characterized as shown: 0.05% of free phenol; viscosity of 8,300 cps (125° C.), 684 cps (150° C.); Mw/Mn 857/360; no phenoxy compound was detected ; and 5.5% of phenol-dicyclopentadiene compound.

EXAMPLE 54

Heating Low Viscosity Dicyclopentadiene/Phenol Condensate with Oxalic Acid

A 250 ml flask with magnetic stir bar was charged with 100 g of condensate with viscosity of 357 cps (25° C.) (experimental equivalent to product of Example 36) and 0.5 g oxalic acid dihydrate. Under nitrogen blanket the reaction was heated 2 hours at 130° C. at which time the viscosity had increased to 798 cps (25° C.). Thirty grams of the reaction mixture was then placed in a 125 ml flask and under vacuum (28.75 inches) heated over 1.25 hours to 160° C. and then this temperature was maintained for 2 hours whereupon the viscosity was 1,000 cps (45° C.). Molecular weights (Mw/Mn) of starting condensate, after 130° C., and 160° C. treatments are 158/147,188/155, and 362/204 respectively. These values of Mw/Mn exclude the phenoxy-dicyclopentadiene compound from calculation of molecular weight. The Mw/Mn values which include the SEC peak at 95±1 are 131/111; 151/118; and 276/149, respectively.

What is claimed is:

1. A method for making a condensation product of a hydroxyaryl and a non-conjugated diene which comprises preparing a reaction medium comprising a hydroxyaryl, a non-conjugated diene, trifluoromethanesulfonic acid and a sufficient quantity of a retarder substance which decreases but does not eliminate the catalytic activity of the acid in the reaction medium and heating the reaction medium at a temperature and time sufficient to effectuate reaction of the diene with the hydroxyaryl wherein the quantity of trifluoromethanesulfonic acid is from about 0.01% to about 1% based on the weight of hydroxyaryl and the quantity of retarder is from about 0.5 to 10 parts by weight for each part by weight of the trifluoromethanesulfonic acid and provided that water is added to the reaction medium when the retarder is solely water.

2. The method of claim 1 wherein the retarder has a pH of about 6 to about 7.5, the quality of the retarder is from about 0.5 to 10 parts by weight for each part of the acid and the heating is conducted for about 1 to 15 hours.

3. The method of claim 1 wherein the retarder is member selected from the group consisting of water, an organic compound and mixtures thereof.

4. The method of claim 3 wherein the organic compound is a member selected from the group consisting of a nitrogen containing compound, an alcohol, an ether and mixtures thereof.

5. The method of claim 4 wherein the nitrogen containing compound is an amide.

6. The method of claim 4 wherein the nitrogen containing compound is an amine having a pKa of about −2 to about 1.2.

7. The method of claim 1 wherein the hydroxyaryl is phenol.

8. The method of claim 1 wherein the diene is dicyclopentadiene.

9. The method of claim 1 wherein the diene is d-limonene.

10. The method of claim 1 wherein the hydroxyaryl is phenol and the diene is dicyclopentadiene or d-limonene.

11. A method for preparing a condensation product of a hydroxyaryl and a non-conjugated diene which comprises contacting a non-conjugated diene with a hydroxyaryl in the presence of a catalyst system consisting essentially of trifluoromethanesulfonic acid and a quantity of a retarder sufficient to decrease but not eliminate the catalytic activity of the acid provided that when the retarder is solely water, the quantity of water is greater than the total moisture content of non-anhydrous non-conjugated diene, hydroxyaryl and trifluoromethanesulfonic acid.

12. A method for preparing a condensation product of a hydroxyaryl and a non-conjugated diene which comprises contacting a reaction mixture of a non-conjugated diene with a hydroxyaryl in the presence of a homogeneous catalyst system comprising trifluoromethanesulfonic acid and a retarder which is a base in relation to the acid in an amount of said retarder which decreases but does not eliminate the catalytic activity of the acid, provided that when the retarder is solely water, water is added to the reaction mixture.

13. A method for producing a condensate of a non-conjugated diene and a hydroxyaryl which comprises forming a reaction mixture by:

(a) contacting from about 0.1 to about 0.8 moles of the diene for each mole of the hydroxyaryl with a catalyst system comprising about 0.01% to about 1% of trifluoromethanesulfonic acid, based on the weight of hydroxyaryl, and from about 0.5 to about 10 times the weight of the acid of a retarder in an amount which decreases without eliminating the catalytic activity of the acid; and (b) heating the reaction mixture at a temperature of about 35° C. to about 190° C. for a time sufficient to effectuate reaction of the hydroxyaryl with the diene.

14. The method of claim 13 wherein the retarder for decreasing the catalytic activity is an organic substance.

15. The method of claim 14 wherein the organic substance is a polymer.

16. The method of claim 14 wherein the organic substance is a member selected from the group consisting of: acetanilide; bis(2-methoxyethyl)ether; N-methyl pyrrolidone; 2-chloropyridine; poly(2-vinyl pyrrolidone); N-cyclohexyl pyrrolidone; and 2-nitroaniline; and the diene is a member selected from the group consisting of dicyclopentadiene and limonene and the hydroxyaryl is a member selected from the group consisting of phenol, a cresol, bisphenol-A, and resorcinol.

17. The method of claim 14 wherein the organic substance is a water soluble polymer.

18. A catalyst composition comprising trifluoromethanesulfonic acid and a retarder in a quantity which decreases but does not eliminate the catalytic activity of the acid in the condensation of a hydroxyaryl with a non-conjugated diene and wherein said retarder: does not react with the double bond of a non-conjugated diene; and is not degraded in the presence of the acid at a temperature of about 80° C.

19. A composition comprising: a hydroxyaryl, a non-conjugated diene, and a homogeneous catalyst system comprising trifluoromethanesulfonic acid and a quantity of a retarder in an amount which decreases, without eliminating, the catalytic activity of the acid in the composition wherein the retarder is an organic substance and the quantity of trifluoromethanesulfonic acid is from about 0.01% to 1% by weight based on the weight of the hyciroxyaryl.

20. A process for making a condensation product of a hydroxyaryl and a non-conjugated diene wherein the product has a ratio of 0.5 to 1.5 of aryloxy-non-conjugated-diene compound to hydroxyaryl-non-conjugated-diene compound and about 40% to at least 90% by weight of the product is said aryloxy-diene compound and said hydroxyaryl-diene compound which comprises:

(a) reacting a non-conjugated diene with a hydroxyaryl at a mole ratio of about 0.2 to about 0.5 moles of the diene for each mole of the hydroxyaryl at a temperature of about 45° C. to about 100° C.

(b) said reaction conducted in the presence of about 0.03% to about 0.1% of trifluoromethanesulfonic acid based on the weight of hydroxyaryl and about 0.03 to about 0.3 of N-methyl pyrrolidone based on the weight of hydroxyaryl, provided that the quantity of the N-methyl pyrrolidone is at least equal to the amount of trifluoromethanesulfonic acid.

21. A composition comprising a condensation product of a hydroxyaryl and a non-conjugated diene, said product including an aryloxy-non-conjugated-diene compound and a hydroxyaryl-non-conjugated-diene compound wherein the ratio of aryloxy-non-conjugated-diene compound to hydroxyaryl-non-conjugated-diene compound in the product is about 0.5 to 1.5 and about 40% to at least 90% by weight of the product is that of said aryloxy-diene compound and said hydroxyaryl-diene compound whereas about 5% by weight to 60% by weight is that of products of the condensation reaction having molecular weights higher than the hydroxyaryl-non-conjugated-diene compound.

22. The composition of claim 21 wherein the aryloxy and hydroxyaryl portions of the diene product are the residue of member selected from the group consisting of phenol, a cresol, bisphenol-A, and resorcinol and the diene portion of the product is the residue of a member selected from the group consisting of dicyclopentadiene and limonene.

23. The product of claim 22 wherein the diene is dicyclopentadiene and the hydroxyaryl is phenol.

24. A process for the preparation of a condensation product of a hydroxyaryl and a non-conjugated diene wherein the product contains at least 90% by weight of an aryloxy-non-conjugated diene compound and a hydroxyaryl-non-conjugated-diene compound and less than about 10% by weight of higher molecular weight products of said condensation which comprises: reacting a non-conjugated diene with a hydroxyaryl in a mole ratio of about 0.3 to 0.5 of non-conjugated diene to hydroxyaryl and at a temperature of about 40° to 70° C. in the presence of, (1). about 0.03% to about 0.1% of trifluoromethanesulfonic acid based on the weight of hydroxyaryl; and (2). about 0.03% to about 0.3% of N-methyl pyrrolidone based on the weight of hydroxyaryl, provided that the quantity of N-methyl pyrrolidone is at least equal to the quantity of the acid.

25. The process of claim 24 wherein the product contains at least 60% by weight of an aryloxy-non-conjugated-diene compound.

26. A composition comprising an aryloxy-non-conjugated-diene compound and a hydroxyaryl-non-conjugated-diene compound wherein the ratio of aryloxy to hydroxyaryl compounds is from about 18 to about 48 by weight and the ratio of said aryloxy and hydroxyaryl compounds to higher molecular weight products of the reaction of a hydroxyaryl and a non-conjugated-diene is at least 9 to 1 by weight.

27. The composition of claim 26 wherein the hydroxyaryl reactant is phenol and the non-conjugated diene reactant is dicyclopentadiene and the condensation product has a viscosity of from about 200 to 400 cps at 25° C.

28. A process for making a condensation product of a hydroxyaryl and a non-conjugated diene wherein the product contains, by weight, from about 5% to about 40% hydroxyaryl-non-conjugated-diene compound, optionally, up to about 2% of aryloxy-non-conjugated-diene compound and products of the condensation having a molecular weight greater than said hydroxyaryl-non-conjugated-diene compound which comprises:

(a) reacting a non-conjugated diene with a hydroxyaryl at a mole ratio of about 0.2 to about 0.5 moles of the diene for each mole of the hydroxyaryl at a temperature of about 130 to about 190° C.;

(b) said reaction conducted in the presence of about 0.03% to about 0.1% of trifluoromethanesulfonic acid based on the weight of hydroxyaryl and about 0.03 to about 0.3 of N-methyl pyrrolidone based on the weight of hydroxyaryl.

29. A composition comprising a condensation product of a hydroxyaryl reactant and a non-conjugated diene reactant wherein the condensation product contains from about 5% to about 40% of a hydroxyaryl-non-conjugated-diene compound, optionally up to 2% of an aryloxy-non-conjugated-diene compound and products of the condensation having a higher molecular weight than the said hydroxyaryl-diene compound, said quantities based on the weight of condensation product.

30. The composition of claim 29 wherein the aryloxy and hydroxyaryl portions of the diene product are the residue of a member selected from the group consisting of phenol, a cresol, bisphenol-A and resorcinol and the diene portion of the product is the residue of a member selected from the group consisting of dicyclopentadiene and limonene.

31. The composition of claim 30 wherein the aryloxy and hydroxyaryl portions are the residue of phenol and the diene portion is the residue of dicyclopentadiene.

32. The composition of claim 18 wherein the quantity of trifluoromethanesulfonic acid is from about 0.03% to 0.15% based on the weight of the hydroxyaryl.

33. A method for making a condensation product of a hydroxyaryl and a non-conjugated diene which comprises reacting a hydroxyaryl with a non-conjugated diene in the presence of from about 0.01 to about 1% of trifluoromethanesulfonic acid by weight based on the weight of the hydroxyaryl and adding water to the hydroxyaryl, diene and acid prior to the reaction, wherein the quantity of added water decreases but does not eliminate the catalytic activity of the acid and then heating the hydroxyaryl, diene and acid at a temperature and time sufficient to effectuate reaction of the diene with the hydroxyaryl.

* * * * *